(12) United States Patent
Kim

(10) Patent No.: US 9,937,240 B2
(45) Date of Patent: Apr. 10, 2018

(54) PEPTIDE HAVING FIBROSIS INHIBITORY ACTIVITY AND COMPOSITION CONTAINING SAME

(71) Applicant: GemVax & KAEL Co., Ltd., Daejeon (KR)

(72) Inventor: Sang Jae Kim, Seoul (KR)

(73) Assignee: GemVax & KAEL Co., Ltd., Daejeon (KR)

( * ) Notice: Subject to any disclaimer, the term of this patent is extended or adjusted under 35 U.S.C. 154(b) by 0 days.

(21) Appl. No.: 15/303,370

(22) PCT Filed: Apr. 10, 2015

(86) PCT No.: PCT/KR2015/003642
§ 371 (c)(1),
(2) Date: Oct. 11, 2016

(87) PCT Pub. No.: WO2015/156649
PCT Pub. Date: Oct. 15, 2015

(65) Prior Publication Data
US 2017/0028035 A1     Feb. 2, 2017

(30) Foreign Application Priority Data

Apr. 11, 2014   (KR) .................. 10-2014-0043586

(51) Int. Cl.
| A61K 38/45 | (2006.01) |
| A61P 29/00 | (2006.01) |
| C12N 9/12  | (2006.01) |
| A61K 31/7068 | (2006.01) |
| A61K 45/06 | (2006.01) |

(52) U.S. Cl.
CPC .......... *A61K 38/45* (2013.01); *A61K 31/7068* (2013.01); *A61K 45/06* (2013.01); *C12N 9/1276* (2013.01); *C12Y 207/07049* (2013.01)

(58) Field of Classification Search
CPC .... A61K 38/45; A61K 31/7068; A61K 45/06; C12N 9/1276; C12Y 207/07049
See application file for complete search history.

(56) References Cited

U.S. PATENT DOCUMENTS

| 6,967,211 | B2 | 11/2005 | Inoue |
| 7,030,211 | B1 | 4/2006 | Gaudernack et al. |
| 7,786,084 | B2 | 8/2010 | Benner et al. |
| 7,794,723 | B2 | 9/2010 | Gaudernack et al. |
| 8,828,403 | B2 | 9/2014 | Filaci et al. |
| 8,933,197 | B2 | 1/2015 | Bogin et al. |
| 9,023,987 | B2 | 5/2015 | Chung et al. |
| 9,540,419 | B2 | 1/2017 | Kim et al. |
| 9,572,858 | B2 | 2/2017 | Kim |
| 2002/0042401 | A1 | 4/2002 | Ferguson et al. |
| 2003/0027769 | A1 | 2/2003 | Scialdone et al. |
| 2003/0143228 | A1 | 7/2003 | Chen et al. |
| 2006/0106196 | A1 | 5/2006 | Gaudernack et al. |
| 2007/0190561 | A1 | 8/2007 | Morin et al. |
| 2008/0025986 | A1* | 1/2008 | Ozes ............... A61K 38/28 424/145.1 |
| 2009/0136917 | A1 | 5/2009 | Szalay et al. |
| 2009/0186802 | A1 | 7/2009 | Alluis et al. |
| 2009/0215852 | A1 | 8/2009 | Bascomb et al. |
| 2011/0135692 | A1 | 6/2011 | Filaci et al. |
| 2011/0150873 | A1 | 6/2011 | Grainger |
| 2011/0183925 | A1 | 7/2011 | Sato et al. |
| 2012/0065124 | A1 | 3/2012 | Morishita et al. |
| 2012/0208755 | A1 | 8/2012 | Leung |
| 2012/0277290 | A1 | 11/2012 | Collard et al. |
| 2013/0129760 | A1 | 5/2013 | Gaudernack et al. |
| 2013/0230591 | A1 | 9/2013 | Fellous et al. |
| 2015/0099692 | A1 | 4/2015 | Kim et al. |
| 2015/0099693 | A1 | 4/2015 | Kim et al. |
| 2015/0175978 | A1 | 6/2015 | Kim |
| 2015/0307859 | A1 | 10/2015 | Kim |

(Continued)

FOREIGN PATENT DOCUMENTS

| EP | 1020190 A3 | 10/2000 |
| EP | 1093381 B2 | 7/2009 |

(Continued)

OTHER PUBLICATIONS

Kyte et al, Telomerase Peptide Vaccination Combined with Temozolomide: A Clinical Trial in Stage IV Melanoma Patients, Clin Cancer Res, 2011, 17, pp. 4568-4580.*
Mandal, Types of Fibrosis, from http://www.news-medical.net/health/Types-of-Fibrosis.aspx, Jul. 3, 2014, pp. 1-3.*
Wynn et al, Mechanisms of fibrosis: therapeutic translation for fibrotic disease, Nature Medicine, 2012, 18, pp. 1028-1040.*
Rosenbloom et al, Strategies for anti-fibrotic therapies, Biochimica et Biophysica Acta, 2013, 1832, pp. 1088-1103.*
Nawroth et al, Intraperitoneal administration of chitosan/DsiRNA nanoparticles targeting TNFa prevents radiation-induced fibrosis, Radiotherapy and Oncology, 2010, 97, pp. 143-148.*
Middleton, G., et al., "Gemcitabine and Capecitabine With or Without Telomerase Peptide Vaccine GV1001 in Patients With Locally Advanced or Metastatic Pancreatic Cancer (TeloVac): an Open-label, Randomised, Phase 3 Trial," The Lancet Oncology 15(8):829-840, Lancet Publishing Group, England (2014).

(Continued)

*Primary Examiner* — Julie Ha
*Assistant Examiner* — Li N Komatsu
(74) *Attorney, Agent, or Firm* — Sterne, Kessler, Goldstein & Fox P.L.L.C.

(57) ABSTRACT

The present invention relates to a composition for inhibiting fibrosis and more specifically, to a composition for inhibiting fibrosis, wherein the composition is effective in inhibiting fibrosis of tissue cells by containing a peptide derived from telomerase. The peptide according to the present invention exhibits an effect of inhibiting the progression of various kinds of fibrosis, including fibrosis due to occurrence of cancer, fibrosis due to the administration of chemotherapy anticancer drugs, fibrosis due to the exposure to radiation, or progressive fibrosis of tissues, including a TGF-β signaling procedure, and thus can provide a composition for anti-fibrosis or inhibiting fibrosis and a method for treating diseases due to fibrosis.

16 Claims, 9 Drawing Sheets

(56) References Cited

U.S. PATENT DOCUMENTS

| | | |
|---|---|---|
| 2015/0343095 A1 | 12/2015 | Kim |
| 2015/0353903 A1 | 12/2015 | Kim |
| 2016/0002613 A1 | 1/2016 | Kim |
| 2016/0008438 A1 | 1/2016 | Kim |
| 2016/0082089 A1 | 3/2016 | Kim |
| 2016/0120966 A1 | 5/2016 | Kim |
| 2016/0137695 A1 | 5/2016 | Kim |
| 2016/0151512 A1 | 6/2016 | Kim |
| 2016/0250279 A1 | 9/2016 | Kim |
| 2016/0296604 A1 | 10/2016 | Kim |
| 2016/0375091 A1 | 12/2016 | Kim |
| 2017/0028035 A1 | 2/2017 | Kim |
| 2017/0058001 A1 | 3/2017 | Kim |
| 2017/0081376 A1 | 3/2017 | Kim et al. |
| 2017/0128557 A1 | 5/2017 | Kim et al. |
| 2017/0143806 A1 | 5/2017 | Kim et al. |
| 2017/0275603 A1 | 9/2017 | Kim et al. |

FOREIGN PATENT DOCUMENTS

| | | | |
|---|---|---|---|
| EP | 1817337 B1 | 1/2011 | |
| JP | 2002522373 A | 7/2002 | |
| JP | 2010252810 A | 11/2010 | |
| JP | 2012526524 A | 11/2012 | |
| JP | 5577472 B2 | 8/2014 | |
| KR | 19930001915 A | 2/1993 | |
| KR | 20010012613 A | 2/2001 | |
| KR | 20010020601 A | 3/2001 | |
| KR | 20040015087 A | 2/2004 | |
| KR | 20040045400 A | 6/2004 | |
| KR | 20040107492 A | 12/2004 | |
| KR | 20050020987 A | 3/2005 | |
| KR | 20050040517 A | 5/2005 | |
| KR | 20060109903 A | 10/2006 | |
| KR | 20070083218 A | 8/2007 | |
| KR | 20080084818 A | 9/2008 | |
| KR | 20090033878 A | 4/2009 | |
| KR | 20090103957 A | 10/2009 | |
| KR | 20100058541 A | 6/2010 | |
| KR | 20100085527 A | 7/2010 | |
| KR | 20110057049 A | 5/2011 | |
| KR | 20110060940 A | 6/2011 | |
| KR | 20110062943 A | 6/2011 | |
| KR | 20110130943 A | 12/2011 | |
| KR | 20120018188 A | 2/2012 | |
| KR | 20120026408 A | 3/2012 | |
| KR | 20120035150 A | 4/2012 | |
| KR | 20120087885 A | 8/2012 | |
| KR | 20120121196 A | 11/2012 | |
| KR | 20120130996 A | 12/2012 | |
| KR | 20120133661 A | 12/2012 | |
| KR | 20130004949 A | 1/2013 | |
| KR | 20130041896 A | 4/2013 | |
| WO | WO-0002581 A1 | 1/2000 | |
| WO | WO-2010003520 A2 | 1/2010 | |
| WO | WO-2010012850 A1 | 2/2010 | |
| WO | WO-2011101173 A1 | 8/2011 | |
| WO | WO-2011150494 A1 | 12/2011 | |
| WO | WO-2013100500 A1 | 7/2013 | |
| WO | WO-2013118899 A1 | 8/2013 | |
| WO | WO-2013135266 A1 | 9/2013 | |
| WO | WO-2013167574 A1 | 11/2013 | |
| WO | WO-2013169060 A1 | 11/2013 | |
| WO | WO-2013169067 A1 | 11/2013 | |
| WO | WO-2013169077 A1 | 11/2013 | |
| WO | WO 2014/012683 A1 * | 1/2014 | ........... C12N 9/1276 |
| WO | WO-2014010971 A1 | 1/2014 | |
| WO | WO-2014046478 A1 | 3/2014 | |
| WO | WO-2014046481 A1 | 3/2014 | |
| WO | WO-2014046490 A1 | 3/2014 | |
| WO | WO-2014171792 A1 | 10/2014 | |
| WO | WO-2014196841 A1 | 12/2014 | |
| WO | WO-2014204281 A1 | 12/2014 | |
| WO | WO-2015060673 A1 | 4/2015 | |
| WO | WO-2015076621 A1 | 5/2015 | |
| WO | WO-2015093854 A1 | 6/2015 | |
| WO | WO-2015167067 A1 | 11/2015 | |
| WO | WO-2016105086 A1 | 6/2016 | |
| WO | WO-2016137162 A1 | 9/2016 | |

OTHER PUBLICATIONS

National Center for Biotechnology Information, "Hormones," MeSH Database, Bethesda, accessed at http://www.ncbi.nlm.nih.gov/mesh/68006728, accessed on May 8, 2017, 3 pages.

NCT00283062, "Adjuvant Leuprolide with or without Docetaxel in High Risk Prostate Cancer After Radical Prostatectomy," accessed at https://clinicaltrials.gov/ct2/show/study/NCT00283062, accessed on May 12, 2017, 7 pages.

NCT00425360, "Gemcitabine, Capecitabine, and Telomerase Peptide Vaccine GV1001 in Treating Patients With Locally Advanced and Metastatic Pancreatic Cancer," as updated on Jan. 22, 2007, ClinicalTrials.gov archive, accessed at https://clinicaltrials.gov/archive/NCT00425360/2007_01_22, accessed on Apr. 7, 2017, 4 pages.

Altschul, S.F., et al., "Basic Local Alignment Search Tool," Journal of Molecular Biology 215(3):403-410, Elsevier, England (1990).

Beer, T.M., et al., "Phase II Study of Weekly Docetaxel in Symptomatic Androgen-independent Prostate Cancer," Annals of Oncology 12(9):1273-1279, Oxford University Press, England (2001).

Bernhardt, S.L., et al., "Telomerase Peptide Vaccination of Patients with Non-Resectable Pancreatic Cancer: A Dose Escalating Phase I/II Study," British Journal of Cancer 95(11):1474-1482, Nature Publishing Group on behalf of Cancer Research, England (2006).

Bohonowych, J.E., et al., "Comparative Analysis of Novel and Conventional HSP90 Inhibitors on HIF Activity and Angiogenic Potential in Clear Cell Renal Cell Carcinoma: Implications for Clinical Evaluation," BMC Cancer 11:520, BioMed Central, England (2011).

Bonaldi, T., et al., "Monocytic Cells Hyperacetylate Chromatin Protein HMGB1 to Redirect it Towards Secretion," The EMBO Journal 22(20):5551-5560, Wiley Blackwell, England (2003).

Brandenburg, K., et al., "Peptide-based Treatment of Sepsis," Applied Microbiology and Biotechnology 90(3):799-808, Springer International, Germany (2011).

Bruns, A.F., et al., "A Heat-shock Protein Axis Regulates VEGFR2 Proteolysis, Blood Vessel Development and Repair," PloS One 7(11):e48539, Public Library of Science, United States (2012).

Brunsvig, P.F., et al., "Telomerase Peptide Vaccination in NSCLC: A Phase II Trial in Stage III Patients Vaccinated after Chemoradiotherapy and an 8-year Update on a Phase I/II Trial," Clinical Cancer Research 17(21):6847-6857, The Association, United States (2011).

Calderwood, S.K., et al., "Heat Shock Proteins in Cancer: Chaperones of Tumorigenesis," Trends in Biochemical Sciences 31(3):164-172, Elsevier Trends Journals, England (2006).

Cho, Y.J., "GemVax & Kael (082270)," Hana Daetoo Securities, Company Report, Sep. 10, 2012, 9 pages.

Choi, S.G., "Recent Advances in Cancer Cachexia," Journal of Korean Oncology Nursing 11(1):20-25 (2011), Abstract only.

Dahlgren, K.N., et al., "Oligomeric and Fibrillar Species of Amyloid-beta Peptides Differentially Affect Neuronal Viability," Journal of Biological Chemistry 277(35):32046-32053, American Society for Biochemistry and Molecular Biology, United States (2002).

Dementia from Merck Manual, accessed on Jul. 29, 2009, pp. 1-17.

Dempsey, N.C., et al., "Differential Heat Shock Protein Localization in Chronic Lymphocytic Leukemia," Journal of Leukocyte Biology 87(3):467-476, Society for Leukocyte Biology, United States (2010).

Dinarello, C.A., "Interleukin-1 in the Pathogenesis and Treatment of Inflammatory Diseases," Blood117(14):3720-3732, American Society of Hematology, United States (2011).

Du, R., et al., "HIF1alpha Induces the Recruitment of Bone Marrow-derived Vascular Modulatory Cells to Regulate Tumor Angiogenesis and Invasion," Cancer Cell 13(3):206-220, Cell Press, United States (2008).

(56) References Cited

OTHER PUBLICATIONS

Engineer, D.R. and Garcia, J.M., "Leptin in Anorexia and Cachexia Syndrome," International Journal of Peptides 2012:Article ID 287457, Hindawi Publishing Corporation, United States (2012).
Eustace, B.K. and Jay, D.G., "Extracellular Roles for the Molecular Chaperone, Hsp90," Cell Cycle 3(9):1098-1100, Taylor & Francis, United States (2004).
Eustace, B.K. and Jay, D.G., "Functional Proteomic Screens Reveal an Essential Extracellular Role for Hsp90 Alpha in Cancer Cell Invasiveness," Nature Cell Biology 6(6):507-514, Macmillan Magazines Ltd., England (2004).
Evans, C.G., et al., "Heat Shock Protein 70 (Hsp70) as an Emerging Drug Target," Journal of Medicinal Chemistry 53(12):4585-4602, American Chemical Society, United States (2010).
Ferrarini, M., et al., "Unusual Expression and Localization of Heat-shock Proteins in Human Tumor Cells," International Journal of Cancer51(4):613-619, Wiley-Liss, United States (1992).
Fire, A., et al., "Potent and Specific Genetic Interference by Double-stranded RNA in Caenorhabditis Elegans," Nature 391(6669):806-811, Nature Publishing Group, England (1998).
Fittipaldi, A., et al., "Cell Membrane Lipid Rafts Mediate Caveolar Endocytosis of HIV-1 Tat Fusion Proteins," Journal of Biological Chemistry 278(36): 34141-34149, American Society for Biochemistry and Molecular Biology, United States (2003).
Fonseca, S.B., et al., "Recent Advances in the Use of Cell-Penetrating Peptides for Medical and Biological Applications," Advanced Drug Delivery Reviews 61(11):953-964, Elsevier Science Publishers, Netherlands (2009).
Fujii, H., et al., "Telomerase Insufficiency in Rheumatoid Arthritis," Proceedings of the National Academy of Sciences USA 106(11):4360-4365, National Academy of Sciences, United States (2009).
Garcia-Carbonero, R., et al., "Inhibition of HSP90 Molecular Chaperones: Moving Into the Clinic," The Lancet Oncology 14(9):e358-e369, Lancet Publishing Group, England (2013).
GemVax Receives Report on Anti-Inflammatory Mechanism, The Asia Economy Daily, Article written on May 7, 2013.
Ghaneh, P., et al., "Biology and Management of Pancreatic Cancer," Gut 56(8):1134-1152, British Medical Association, England (2007).
Granger, D.N. and Korthuis, R.J., "Physiologic Mechanisms of Postischemic Tissue Injury," Annual Review of Physiology 57:311-332, Annual Reviews, United States (1995).
Gunturu, K.S., et al., "Immunotherapy Updates in Pancreatic Cancer: Are we there yet?," Therapeutic Advances in Medical Oncology 5(1):81-89, Sage, England (2013).
Heitz, F., et al., "Twenty Years of Cell-Penetrating Peptides: From Molecular Mechanisms to Therapeutics," British Journal of Pharmacology 157(2):195-206, Wiley, England (2009).
Heldin, C.H., et al., "TGF-Beta Signalling from Cell Membrane to Nucleus through SMAD Proteins," Nature 390(6659):465-471, Nature Publishing Group, England (1997).
Henry, J.Y., et al., "Lenalidomide Enhances the Anti-prostate Cancer Activity of Docetaxel in vitro and in vivo," The Prostate 72(8):856-867, Wiley-Liss, United States (2012).
Hse, "Rheumatoid arthritis," http://www.hse.ie/portal/eng, accessed at http://www.hse.ie/portal/eng/health/az/R/Rheumatoid-arthritis/, 14 pages (2013).
Inderberg-Suso, E.M., et al., "Widespread CD4+ T-cell Reactivity to Novel hTERT Epitopes following Vaccination of Cancer Patients with a Single hTERT Peptide GV1001," Oncoimmunology 1(5):670-686, Taylor and Francis, United States (2012).
International Preliminary Report on Patentability for Application No. PCT/KR2014/004752, The International Bureau of WIPO, Switzerland, dated Nov. 1, 2016, 23 pages.
International Preliminary Report on Patentability for Application No. PCT/KR2015/003642, The International Bureau of WIPO, Switzerland, dated Oct. 12, 2016, 18 pages.
International Preliminary Report on Patentability for International Application No. PCT/KR2014/011280, The International Bureau of WIPO, Geneva, Switzerland, dated May 24, 2016, 15 pages.
International Preliminary Report on Patentability for International Application No. PCT/EP2013/059460, International Bureau of WIPO, Switzerland, dated Nov. 11, 2014, 5 pages.
International Preliminary Report on Patentability for International Application No. PCT/KR2013/004145, The International Bureau of WIPO, Switzerland, dated Nov. 11, 2014,14 pages.
International Preliminary Report on Patentability for International Application No. PCT/KR2013/004176, The International Bureau of WIPO, Switzerland, dated Nov. 11, 2014,14pages.
International Preliminary Report on Patentability for International Application No. PCT/KR2013/006218, The International Bureau of WIPO, Switzerland, dated Jan. 13, 2015,27 pages.
International Preliminary Report on Patentability for International Application No. PCT/KR2013/008438, The International Bureau of WIPO, Switzerland, dated Mar. 24, 2015, 10 pages.
International Preliminary Report on Patentability for International Application No. PCT/KR2013/008445, The International Bureau of WIPO, Switzerland, dated Mar. 24, 2015, 13 pages.
International Preliminary Report on Patentability for International Application No. PCT/KR2014/003425, The International Bureau of WIPO, Switzerland, dated Oct. 20, 2015, 14 pages.
International Preliminary Report on Patentability for International Application No. PCT/KR2014/005031, The International Bureau of WIPO, Switzerland, dated Dec. 8, 2015, 8 pages.
International Preliminary Report on Patentability for International Application No. PCT/KR2014/005508, The International Bureau of WIPO, Switzerland, dated Jan. 5, 2016, 14 pages.
International Preliminary Report on Patentability for International Patent Application No. PCT/KR2013/004156, The International Bureau of WIPO, Geneva, Switzerland, dated Nov. 11, 2014, 15 pages.
International Search Report for International Application No. PCT/KR2014/003425, Korean Intellectual Property Office, Republic of Korea, dated Jul. 21, 2014, 8 pages.
International Search Report for International Application No. PCT/KR2014/011280, Korean Intellectual Property Office, Republic of Korea, dated Feb. 11, 2015, 12 pages.
International Search Report for International Application No. PCT/EP2013/059460, European Patent Office, Netherlands, dated Jul. 3, 2013, 5 pages.
International Search Report for International Application No. PCT/KR2013/004145, Korean Intellectual Property Office, Republic of Korea, dated Aug. 14, 2013, 10 pages.
International Search Report for International Application No. PCT/KR2013/004176, Korean Intellectual Property Office, Republic of Korea, dated Aug. 6, 2013, 10 pages.
International Search Report for International Application No. PCT/KR2013/006218, Korean Intellectual Property Office, Republic of Korea, dated Sep. 26, 2013, 8 pages.
International Search Report for International Application No. PCT/KR2013/008438, Korean Intellectual Property Office, Republic of Korea, dated Dec. 23, 2013, 8 pages.
International Search Report for International Application No. PCT/KR2013/008445, Korean Intellectual Property Office, Republic of Korea, dated Dec. 23, 2013, 10 pages.
International Search Report for International Application No. PCT/KR2014/004752, Korean Intellectual Property Office, Republic of Korea, dated Jan. 16, 2015, 10 pages.
International Search Report for International Application No. PCT/KR2014/005031, Korean Intellectual Property Office, Republic of Korea, dated Sep. 22, 2014, 6 pages.
International Search Report for International Application No. PCT/KR2014/005508, Korean Intellectual Property Office, Republic of Korea, dated Oct. 14, 2014, 8 pages.
International Search Report for International Application No. PCT/KR2014/010035, Korean Intellectual Property Office, Republic of Korea, dated Feb. 2, 2015, 8 pages.
International Search Report for International Application No. PCT/KR2015/003642, Korean Intellectual Property Office, Republic of Korea, dated Jul. 3, 2015, 8 pages.
International Search Report for International Patent Application No. PCT/KR2013/004156, Korean Intellectual Property Office, Republic of Korea, dated Aug. 14, 2013, 10 pages.

(56) References Cited

OTHER PUBLICATIONS

International Search Report for International Application No. PCT/KR2014/012502, Korean Intellectual Property Office, Republic of Korea, dated on Mar. 11, 2015, 10 pages.
International Search Report for International Application No. PCT/KR2013/008459, Korean Intellectual Property Office, Republic of Korea, dated Dec. 23, 2013, 8 pages.
International Preliminary Report on Patentability for International Application No. PCT/KR2014/012502, The International Bureau of WIPO, Geneva, Switzerland, dated Jun. 21, 2016, 22 pages.
Jaattela, M., "Over-expression of Hsp70 Confers Tumorigenicity to Mouse Fibrosarcoma Cells," International Journal of Cancer 60(5):689-693, Wiley-Liss, United States (1995).
Jemal, A., et al., "Cancer Statistics, 2008," CA: A Cancer Journal for Clinicians 58(2):71-96, Wiley, United States (2008).
Kern, K.A. and Norton, J.A., "Cancer Cachexia," Journal of Parenteral and Enteral Nutrition 12(3):286-298, Sage Publications, United States (1988).
Kim, B.K., et al., "Tumor-suppressive Effect of a Telomerase-derived Peptide by Inhibiting Hypoxia-induced HIF-1α-VEGF Signaling Axis," Biomaterials 35(9):2924-2933, Elsevier Science, Netherlands (2014).
Kim, H.O. and Lee, S.I., "Experimental Animal Models for Rheumatoid Arthritis: Methods and Applications," Journal of Rheumatic Diseases 19(4):189-195, The Korean College of Rheumatology, Republic of Korea(2012), Abstract only.
Kocsis, J., et al., "Serum Level of Soluble 70-kD Heat Shock Protein Is Associated With High Mortality in Patients With Colorectal Cancer Without Distant Metastasis," Cell Stress & Chaperones 15(2):143-151, Springer, Netherlands (2010).
Kokhaei, P., et al., "Telomerase (hTERT 611-626) Serves as a Tumor Antigen in B-cell Chronic Lymphocytic Leukemia and Generates Spontaneously Antileukemic, Cytotoxic T Cells," Experimental Hematology 35(2):297-304, Elsevier Science Inc., Netherlands (2007).
Kyte, J.A., "Cancer Vaccination with Telomerase Peptide GV1001," Expert Opinion on Investigational Drugs 18(5):687-694, Taylor & Francis, England (2009).
Lahdevirta, J., et al., "Elevated Levels of Circulating Cachectin/tumor Necrosis Factor in Patients with Acquired Immunodeficiency Syndrome," American Journal of Medicine 85(3):289-291, Excerpta Medica, United States (1988).
Laviano, A., et al., "Therapy Insight: Cancer Anorexia-cachexia Syndrome—When All You Can Eat is Yourself," Nature Clinical Practice. Oncology 2(3):158-165, Nature Publishing Group, England (2005).
Lee, S.A., et al., "Heat Shock Protein-Mediated Cell Penetration and Cytosolic Delivery of Macromolecules by a Telomerase-Derived Peptide Vaccine," Biomaterials 34(30):7495-7505, Elsevier Science, Netherlands (2013).
Liu, Q.J., et al., "Rapamycin Enhances the Susceptibility of Both Androgen-dependent and- independent Prostate Carcinoma Cells to Docetaxel," Chinese Medical Journal 123(3):356-360, Chinese Medical Association, China (2010).
Luft, R., et al., "A Case of Severe Hypermetabolism of Nonthyroid Origin with a Defect in the Maintenance of Mitochondrial Respiratory Control: A Correlated Clinical, Biochemical, and Morphological Study," Journal of Clinical Investigation 41:1776-1804, American Society for Clinical Investigation, United States (1962).
Martinez, P. and Blasco, M.A., "Telomeric and Extra-telomeric Roles for Telomerase and the Telomere-binding Proteins," Nature Reviews Cancer 11(3):161-176, Nature Publishing Group, England (2011).
Massague, J., "Tgf-Beta Signal Transduction," Annual Review of Biochemistry 67:753-791, Annual Reviews, United States (1998).
Mattson, M.P., "Pathways Towards and Away From Alzheimer's Disease," Nature 430(7000):631-639, Nature Publishing Group, England (2004).
McConnell, J.D., et al., "The Effect of Finasteride on the Risk of Acute Urinary Retention and the Need for Surgical Treatment Among Men with Benign Prostatic Hyperplasia. Finasteride Long-term Efficacy and Safety Study Group," The New England Journal of Medicine 338(9):557-563, Massachusetts Medical Society, United States (1998).
Modica-Napolitano, J.S. and Singh, K.K., "Mitochondria as Targets for Detection and Treatment of Cancer," Expert Reviews in Molecular Medicine 4(9):1-19, Cambridge University Press, England (2002).
Morano, K.A., "New Tricks for an Old Dog: the Evolving World of Hsp70," Annals of the New York Academy of Sciences 1113:1-14, Blackwell, United States (2007).
Murphy, M.E., "The Hsp70 Family and Cancer," Carcinogenesis 34(6):1181-1188, Irl Press, England (2013).
Myers, L.K., et al., "Collagen-Induced Arthritis, an Animal Model of Autoimmunity," Life Sciences 61(19):1861-1878, Elsevier, Netherlands (1997).
Nagaraju, G.P., et al., "Antiangiogenic Effects of Ganetespib in Colorectal Cancer Mediated Through Inhibition of HIF-1α and STAT-3," Angiogenesis 16(4):903-917, Springer, Germany (2013).
National Horizon Scanning Centre News on Emerging Technologies in Healthcare, GV1001 for Advanced and/or Metastatic Pancreatic Cancer, Published Apr. 2008.
NCBI, Reference Sequence: XP_003776612.1 (Jul. 17, 2012).
Novina, C.D. and Sharp, P.A., "The RNAi Revolution," Nature 430(6996):161-164, Nature Publishing Group, England (2004).
Oh, H., et al., "Telomerase Reverse Transcriptase Promotes Cardiac Muscle Cell Proliferation, Hypertrophy, and Survival," Proceedings of the National Academy of Sciences USA 98(18):10308-10313, National Academy of Sciences, United States (2001).
Pearson, W.R. and Lipman, D.J., "Improved Tools for Biological Sequence Comparison," Proceedings of the National Academy of Sciences USA 85(8):2444-2448, National Academy of Sciences, United States (1988).
Perez, R.G., et al., "The Beta-amyloid Precursor Protein of Alzheimer's Disease Enhances Neuron Viability and Modulates Neuronal Polarity," The Journal of Neuroscience 17(24):9407-9414, Society for Neuroscience, United States (1997).
Pfosser, A., et al., "Liposomal HSP90 Cdna Induces Neovascularization via Nitric Oxide in Chronic Ischemia," Cardiovascular Research 65(3):728-736, Oxford Journals, England (2005).
Powers, M.V., et al., "Targeting HSP70: the Second Potentially Druggable Heat Shock Protein and Molecular Chaperone?," Cell Cycle 9(8):1542-1550, Taylor & Francis, United States (2010).
Rana, T.M., "Illuminating the Silence: Understanding the Structure and Function of Small RNAs," Nature Reviews. Molecular Cell Biology 8(1):23-36, Nature Publishing Group, England (2007).
Rheumatoid Arthritis from Merck Manual, accessed on Apr. 21, 2016, pp. 1-18.
Roubenoff, R., et al., "Adjuvant Arthritis as a Model of Inflammatory Cachexia," Arthritis and Rheumatism 40(3):534-539, Wiley-Blackwell, United States (1997).
Sayers, S., et al., "Vaxjo: A Web-based Vaccine Adjuvant Database and its Application for Analysis of Vaccine Adjuvants and their Uses in Vaccine Development," Journal of Biomedicine and Biotechnology 2012:1-13, Article ID 831486, Hindawi Publishing Corporation, United States (2012).
Schenk, D., et al., "Immunization with Amyloid-beta Attenuates Alzheimer-disease-like Pathology in the PDAPP Mouse," Nature 400(6740):173-177, Nature Publishing Group, England (1999).
Schlapbach, C., et al., "Telomerase-specific GV1001 Peptide Vaccination Fails to Induce Objective Tumor Response in Patients with Cutaneous T Cell Lymphoma," Journal of Dermatological Science 62(2):75-83, Elsevier, Netherlands (2011).
Seo, J.S., et al., "T Cell Lymphoma in Transgenic Mice Expressing the Human Hsp70 Gene," Biochemical and Biophysical Research Communications 218(2):582-587, Elsevier, United States (1996).
Shay, J.W., and Wright, W.E., "Telomerase Therapeutics for Cancer: Challenges and New Directions," Nature Reviews. Drug Discovery 5(7):577-584, Nature Publishing Group, England (2006).
Smith, D.B. and Johnson, K.S., "Single-step Purification of Polypeptides Expressed in *Escherichia coli* as Fusions with Glutathione S-transferase," Gene 67(1):31-40, Elsevier, Netherlands (1988).

(56) References Cited

OTHER PUBLICATIONS

Smith, T.F. and Waterman, M.S., "Comparison of Biosequences," Advances in Applied Mathematics 2(4):482-489, Academic Press, Inc., United States (1981).
Song, J., et al., "Characterization and Fate of Telomerase-Expressing Epithelia during Kidney Repair," Journal of the American Society of Nephrology 22(12):2256-2265, American Society of Nephrology, United States (2011).
Southern Cross, "Rheumatoid arthritis—causes, symptoms, and treatment," https://www.southerncross.co.nz/, accessed at https://www.southerncross.co.nz/AboutTheGroup/HealthResources/MedicalLibrary/tabid/178/vw/1/itemID/124/Rheumatoid-arthritis-causes-symptoms-treatment.aspx, last reviewed on May 31, 2013, 5 pages.
Stevenson, C.L., "Advances in Peptide Pharmaceuticals," Current Pharmaceutical Biotechnology 10(1):122-137, Bentham Science Publishers, United Arab Emirates (2009).
Sun, J., et al., "Induction of Angiogenesis by Heat Shock Protein 90 Mediated by Protein Kinase Akt and Endothelial Nitric Oxide Synthase," Arteriosclerosis, Thrombosis, and Vascular biology 24(12):2238-2244, Lippincott Williams & Wilkins, United States (2004).
Taylor, P.C. and Feldmann, M., "Anti-TNF Biologic Agents: Still the Therapy of Choice for Rheumatoid Arthritis," Nature Reviews. Rheumatology 5(10):578-582, Macmillan Publishers Limited, England (2009).
Thompson, J.D., et al., "Clustal W: Improving the Sensitivity of Progressive Multiple Sequence Alignment Through Sequence Weighting, Position-specific Gap Penalties and Weight Matrix Choice," Nucleic Acids Research 22(22):4673-4680, Oxford University Press, England (1994).
Tisdale, M.J., "Mechanisms of Cancer Cachexia," Physiological Reviews 89(2):381-410, American Physiological Society, United States (2009).
Tomari Y. and Zamore, P.D., "Perspective: Machines for RNAi," Genes and Development 19(5):517-529, Cold Spring Harbor Laboratory Press, United States (2005).
Uehara, Y., "Natural Product Origins of Hsp90 Inhibitors," Current Cancer Drug Targets 3(5):325-330, Bentham Science Publishers, Netherlands (2003).
Van Coppenolle, F., et al., "Effects of Hyperprolactinemia on Rat Prostate Growth: Evidence of Androgeno-dependence," American Journal of Physiology. Endocrinology and Metabolism 280(1):E120-E129, American Physiological Society, United States (2001).
Vanbuskirk, A., et al., "A Peptide Binding Protein Having a Role in Antigen Presentation Is a Member of the HSP70 Heat Shock Family," The Journal of Experimental Medicine 170(6):1799-1809, Rockefeller University Press, United States (1989).
Vennela, B., et al., "Current and Future Strategies for Therapy of Pancreatic Cancer," International Journal of Research in Pharmacy and Medicine 2(3):728-740 (2012).
Volloch, V.Z. and Sherman, M.Y., "Oncogenic Potential of Hsp72," Oncogene 18(24):3648-3651, Nature Publishing Group, England (1999).
Walsmith, J. and Roubenoff, R., "Cachexia in Rheumatoid Arthritis," International Journal of Cardiology 85(1):89-99, Elsevier, Netherlands (2002).
Wang, W., et al., "Alleviating the Ischemia-Reperfusion Injury of Donor Liver by Transfection of Exogenous hTERT Genes," Transplantation Proceedings 41(5):1499-1503, Elsevier Science, United States (2009).
Written Opinion for International Application No. PCT/KR2014/011280, Korean Intellectual Property Office, Republic of Korea, dated Feb. 11, 2015, 14 pages.
Written Opinion for International Application No. PCT/EP2013/059460, European Patent Office, Germany, dated Jul. 3, 2013, 4 pages.
Written Opinion for International Application No. PCT/KR2013/004145, Korean Intellectual Property Office, Republic of Korea, dated Aug. 14, 2013, 13 pages.
Written Opinion for International Application No. PCT/KR2013/004176, Korean Intellectual Property Office, Republic of Korea, dated Aug. 6, 2013, 13 pages.
Written Opinion for International Application No. PCT/KR2013/006218, Korean Intellectual Property Office, Republic of Korea, dated Sep. 26, 2013, 26 pages.
Written Opinion for International Application No. PCT/KR2013/008438, Korean Intellectual Property Office, Republic of Korea, dated Dec. 23, 2013, 9 pages.
Written Opinion for International Application No. PCT/KR2013/008445, Korean Intellectual Property Office, Republic of Korea, dated Dec. 23, 2013, 12 pages.
Written Opinion for International Application No. PCT/KR2014/004752, Korean Intellectual Property Office, Republic of Korea, dated Jan. 16, 2015, 21 pages.
Written Opinion for International Application No. PCT/KR2014/005031, Korean Intellectual Property Office, Republic of Korea, dated Sep. 22, 2014, 7 pages.
Written Opinion for International Application No. PCT/KR2014/005508, Korean Intellectual Property Office, Republic of Korea, dated Oct. 14, 2014, 13 pages.
Written Opinion for International Application No. PCT/KR2015/003642, Korean Intellectual Property Office, Republic of Korea, dated Jul. 3, 2015, 16 pages.
Written Opinion for International Application No. PCT/KR2013/008459, Korean Intellectual Property Office, Republic of Korea, dated Dec. 23, 2013, 9 pages.
Written Opinion for International Patent Application No. PCT/KR2013/004156, Korean Intellectual Property Office, Republic of Korea, dated Aug. 14, 2013, 13 pages.
Written Opinion for International Application No. PCT/KR2014/003425, Korean Intellectual Property Office, Republic of Korea, dated Jul. 21, 2014, 13 pages.
Written Opinion for International Application No. PCT/KR2014/012502, Korean Intellectual Property Office, Republic of Korea, dated Mar. 11, 2015, 20 pages.
Yankner, B.A., et al., "Neurotrophic and Neurotoxic Effects of Amyloid Beta Protein: Reversal by Tachykinin Neuropeptides," Science 250(4978):279-282, American Association for the Advancement of Science, United States (1990).
Yeh, C.H., et al., "Clinical Correlation of Circulating Heat Shock Protein 70 in Acute Leukemia," Leukemia Research 34(5):605-609, Pergamon Press, England (2010).
Yi, A., et al., "Radiation-Induced Complications after Breast Cancer Radiation Therapy: a Pictorial Review of Multimodality Imaging Findings," Korean Journal of Radiology 10(5):496-507, Korean Society of Radiology, Korea (2009).
Zhang, H., et al., "Inhibiting TGFβ1 has a Protective Effect on Mouse Bone Marrow Suppression Following Ionizing Radiation Exposure in Vitro," Journal of Radiation Research 54(4):630-636, Oxford University Press, England (2013).
Zhou, J., et al., "PI3K/Akt Is Required for Heat Shock Proteins to Protect Hypoxia-inducible Factor 1alpha From pVHL-independent Degradation," The Journal of Biological Chemistry 279(14):13596-13513, American Society for Biochemistry and Molecular Biology, United States (2004).
Co-pending U.S. Appl. No. 15/307,632, inventors Kim, Sang Jae, filed Oct. 28, 2016 (Not Yet Published).
Co-pending U.S. Appl. No. 15/346,870, inventors Kim, Sang Jae, filed Nov. 9, 2016 (Not Yet Published).
Eisenegger, C., et al., "The Role of Testosterone in Social Interaction," Trends in Cognitive Sciences 15(6):263-271, Elsevier Science, England (2011).
"Seoul National University Bundang Hospital excited because of '000'," Clinical trials of Dream Anticancer Drug without side effects with Kael & GemVax, 4 pages, Apr. 22, 2013.
Gong, W., et al., "Invasion Potential of H22 Hepatocarcinoma Cells is Increased by HMGB1-induced Tumor NF-κB Signaling via Initiation of HSP70," Oncology Reports 30(3):1249-1256, D.A. Spandidos, Greece (2013).

(56) References Cited

OTHER PUBLICATIONS

Guo, R.F., et al., "Regulatory Effects of Eotaxin on Acute Lung Inflammatory Injury," Journal of Immunology 166(8):5208-5218, American Association of Immunologists, United States (2001).

International Preliminary Report on Patentability for International Application No. PCT/KR2014/010035, Korean Intellectual Property Office, Republic of Korea, dated Apr. 26, 2016, 13 pages.

Kawasaki, H., et al., "Detection and Evaluation of Activation of Various Cancer Antigenic Peptide-specific CTLs in Mature Dendritic Cells Used for Dendritic Cell Therapy," The 21st International Congress of Personalized Medicine, Conference Program and Abstracts, Personalized Medicine Universe (Japanese edition) 4(Supplement 2): 2 pages, Oct. 17, 2015.

Morishita, M., and Peppas, N.A., "Is the Oral Route Possible for Peptide and Protein Drug Delivery?," Drug Discovery Today 11(19-20):905-910, Elsevier Science Ltd., England (2006).

National Institute of Diabetes and Digestive and Kidney Diseases, "Prostate Enlargement: Benign Prostatic Hyperplasia," Updated Sep. 2014, 14 pages.

Sasada, A., et al., "A Case of Elderly Patient With Lung Cancer Efficiently Treated With Dendritic Cell Immunotherapy," The 20th International Congress of Personalized Medicine, Conference Program and Abstracts, Personalized Medicine Universe (Japanese edition) 4(Supplement 1): 2 pages, May 24, 2015.

Shaw, V.E., et al., "Current Status of GV1001 and Other Telomerase Vaccination Strategies in the Treatment of Cancer," Expert Review of Vaccines 9(9):1007-1016, Taylor & Francis, England (2010).

Written Opinion for International Application No. PCT/KR2014/010035, Korean Intellectual Property Office, Republic of Korea, dated Feb. 2, 2015, 11 pages.

Co-pending U.S. Appl. No. 15/539,396, inventors Kim, S.J., et al., I.A. filed Dec. 22, 2015 (Not Published).

Co-pending U.S. Appl. No. 15/553,689, inventors Kim, S.J., et al., I.A. filed Feb. 18, 2016 (Not Published).

De Araujo, J.G., et al., "The Potential Use of Melatonin for Preventing Cisplatin Ototoxicity: An Insight for a Clinical Approach," Advances in Otolaryngology Article ID 185617, 8 pages, Hindawi Publishing Corporation (2014).

International Preliminary Report on Patentability and Written Opinion for International Application No. PCT/KR2015/014099, The International Bureau of WIPO, dated Jun. 27, 2017, 16 pages.

International Search Report for International Application No. PCT/KR2015/014099, Korean Intellectual Property Office, Republic of Korea, dated May 4, 2016, 8 pages.

International Search Report for International Application No. PCT/KR2016/001646, Korean Intellectual Property Office, Republic of Korea, dated May 20, 2016, 8 pages.

Kim, B-H., "Presbycusis: Review for its Environmental Risk Factors," Korean Journal of Otorhinolaryngology—Head and Neck Surgery 49(10):962-967, Korean Society of Otolaryngology—Head and Neck Surgery, Korea (2006), Abstract only.

Kyte, J.A., et al., "Telomerase Peptide Vaccination Combined with Temozolomide: A Clinical Trial in Stage IV Melanoma Patients," Clinical Cancer Research 17(13):4568-4580, American Association of Cancer Research, United States (2011).

Lee, E.K., et al., "Inhibition of Experimental Choroidal Neovascularization by Telomerase-derived Peptide GV1001," Investigative Ophthalmology & Visual Science 56(7):Abstract 2291, ARVO Annual Meeting Abstract (Jun. 2015), 2 pages.

Priya, S.G., et al., "Skin Tissue Engineering for Tissue Repair and Regeneration," Tissue Engineering. Part B, Reviews 14(1):105-118, Mary Ann Liebert, Inc., United States (2008).

Rowe-Rendleman, C. and Glickman, R.D., "Possible therapy for age-related macular degeneration using human telomerase," Brain Research Bulletin 62(6):549-553, Elsevier Science Inc., United States (2004).

Tisdale, M.J., "Catabolic Mediators of Cancer Cachexia," Current Opinion in Supportive and Palliative Care, 2(4):256-261, Lippincott Williams & Wilkins, United States (2008).

Westin, E.R., et al., "The $p53/p21^{WAF/CIP}$ Pathway Mediates Oxidative Stress and Senescence in Dyskeratosis Congenita Cells With Telomerase Insufficiency," Antioxidants & Redox Signaling 14(6):985-997, Mary Ann Liebert, Inc., United States (2011).

International Preliminary Report on Patentability and Written Opinion for International Application No. PCT/KR2016/001646, Korean Intellectual Property Office, Republic of Korea, dated May 20, 2016, 13 pages.

* cited by examiner

*In vivo* anti-tumor effects of PEP1 combined with Gemcitabine:
Weight Changes (AsPC1)

ASPC1. Control (without Gemcitabine & PEP1)

ASPC1 + PEP1

ASPC1 + Gemcitabine

ASPC1 + Gemcitabine + PEP1

PEPTIDE HAVING FIBROSIS INHIBITORY ACTIVITY AND COMPOSITION CONTAINING SAME

CROSS-REFERENCE TO RELATED APPLICATIONS

This application is a U.S. national phase entry of PCT/KR2015/003642, filed Apr. 10, 2015, which claims foreign priority to KR 10-2014-0043566, filed Apr. 11, 2014, each of which is incorporated by reference herein in its entirety.

BACKGROUND OF THE INVENTION

Technical Field

The present invention relates to a peptide having an anti-fibrosis effect and a composition including the same, and more particularly, to an anti-fibrosis composition which includes a telomerase-derived peptide and thus is effective in inhibiting the occurrence of fibrosis of various types of tissue cells.

Background Art

Fibrosis is a disease eliciting abnormal formation, accumulation and precipitation of an extracellular matrix, caused by fibroblasts, and refers to abnormal accumulation of a collagen matrix due to injury or inflammation that changes the structures and functions of various types of tissue. Regardless of where fibrosis arises, most aetiology of fibrosis includes excessive accumulation of a collagen matrix substituting normal tissue. Particularly, fibrosis occurring in the kidney, liver, lung, heart, bone or bone marrow, and skin induces organ failure and leads to death at worst. The fibroblast serves to form fibrous tissue by producing an extracellular matrix precursor in a normal state. The extracellular matrix, which is a material between cells in connective tissue, exists in the form of a protein such as fibronectin, laminin, chondronectin or collagen.

Meanwhile, TGF-β plays various roles in the abnormal formation and accumulation of the extracellular matrix caused by fibroblasts, cell proliferation, inflammation, and cancer cell metastasis, and many cellular signaling pathways and targets have been identified. Accordingly, in many disease models, TGF-β has been studied, and fields in which the study on TGF-β and development of related drugs are most active may be fibrotic diseases and cancer.

In the TGF-β mechanism, generally, TGF-β binds to a TGF-β receptor to induce phosphorylation of Smad proteins in the cytoplasm and transfers signals through interactions with various Smad proteins. Here, Smad2 and Smad3 are usually involved, and Smad1 and Smad5 are involved in bone morphogenic protein (BMP) signaling. In addition, Smad4 is known as a common signaling substance involved in activin and BMP, as well as TGF-β (Heldin, C H et al. *Nature*, 1997, 390, 465-471; Massague *J. Annu. Rev. Biochem.* 1998, 67, 753-791).

As inhibition of tumor invasion and epithelial-mesenchymal transition (EMT) are regulated by inhibition of the TGF-β signaling mechanism, excellent anticancer therapeutic effects can be expected. Moreover, considering that TGF-β is the critical cytokine in the regulation of cell proliferation and differentiation, it has also attracted attention as a therapeutic method for preventing fibrosis caused by radiation, which is mentioned as the main side effect of an anticancer treatment (Zhang et al. *J Radiat Res.* 2013, 54, 630-636).

Recently, ESBRIET® (Pirfenidone) approved by the FDA (Oct. 15, 2014) as a therapeutic agent for idiopathic pulmonary fibrosis is a TGF-β inhibitor, which is known to have inhibition of TGF-β formation as a main action mechanism. Also, it has been reported that TGF-β is a cell proliferation regulatory factor, which induces or suppresses cell proliferation and thus plays an important role in pathogenesis of various diseases including cancer, cardiac diseases, and diabetes, and various physiological activities thereof have also been reported. For example, ESBRIET® (Pirfenidone) acts as an inhibitor against TGF-β synthesis (inhibition of forming a cell proliferation regulatory factor), a TGF-β antagonist (disturbance of a TGF receptor, signaling disturbance), a PDGF (platelet-derived growth factor) antagonist (inhibition of angiogenesis inducing factor), a p38 MAP kinase inhibitor (inhibition of cell proliferation signaling enzyme), and an anti-inflammatory agent (inhibition of formation of TNF-alpha and MAPK). Therefore, if a new pharmaceutical composition can be developed that is effective in directly inhibiting TGF-β or blocking a TGF-β-involved signaling process and even has no side effect, such a pharmaceutical composition can prevent and treat various diseases and senescence, which are caused by fibrosis.

Particularly, in a cancer environment, there are various fibrosis-causing factors such as cancer tissue, anticancer agents, and radiation therapy, and therefore fibrosis inhibition has more significance in the cancer environment. Today's most popular anticancer treatments, radiation therapy and chemotherapy are known to considerably attenuate the quality of life of a patient and severely worsen prognosis of the anticancer treatment due to side effects caused by fibrosis and the like.

For this reason, there is a demand for developing a therapeutic agent for inhibiting the cancer-associated TGF-β signaling mechanism which will be useful for not only developing anticancer vaccines but also being new therapeutic agents and methods for maximizing effects of conventional anticancer treatment. For instance, in anticancer treatment, fibrosis caused by cancer tissue, an anticancer agent, or radiation exposure interferes with delivery and efficacy of a drug designed to exhibit an anticancer effect when an anticancer agent is delivered to a cancerous region and prevents effective anticancer treatment by blocking transfer of anticancer immune cells to the cancerous region. Therefore, if a new pharmaceutical composition which has no side effect on a human body and is able to inhibit fibrosis caused by cancer tissue, a chemotherapeutic agent, or radiation exposure, anticancer treatment may be more effectively performed.

PRIOR ART DOCUMENTS

Patent Documents (Patent Document 0001) KR1019930001915 A
(Patent Document 0002) KR1020040107492 A

DETAILED DESCRIPTION OF THE INVENTION

Technical Problem

With the background described above, the inventors attempted to develop an anti-fibrosis composition having excellent effects without a side effect and thus, completed the present invention.

An object of the present invention is to provide an effective anti-fibrosis composition.

Technical Solution

In one aspect, the present invention provides an anti-fibrosis composition, which includes at least one selected from the group consisting of a peptide comprising an amino acid sequence of SEQ. ID. NO: 1 (hereinafter, referred to as "PEP1"), a peptide having 80% or higher sequence homology with the amino acid sequence, and a fragment thereof.

In the composition according to the present invention, the fragment of the peptide may be a fragment consisting of three or more amino acids.

In the composition according to the present invention, the fibrosis may be fibrosis induced by at least one selected from the group consisting of cancer, administration of an anti-cancer agent, and exposure to radiation.

In the composition according to the present invention, the composition may inhibit fibrosis of cancer cell tissue selected from the group consisting of pancreatic cancer, colorectal cancer, stomach cancer, prostate cancer, non-small cell lung cancer, breast cancer, melanoma and ovarian cancer.

In the composition according to the present invention, the composition may be used in combination with a chemotherapeutic agent or a radiation therapy to inhibit fibrosis of cancer tissue. The chemotherapeutic agent may be at least one selected from deoxynucleoside analogs and fluoropyrimidines, wherein the deoxynucleoside analog may be gemcitabine, and the fluoropyrimidine may be 5-fluorouracil or capecitabine.

In the composition according to the present invention, the composition may be a pharmaceutical composition further including pharmaceutically acceptable excipients and additives.

In the composition according to the present invention, the composition may be an anti-fibrosis composition involved in a TGF-β signaling process and therefore inhibiting fibrosis of dermal tissue.

In the composition according to the present invention, the composition may further include acceptable excipients, lubricants and additives, and may be a cosmetic composition.

In another aspect, the present invention provides a method for treating and preventing a fibrotic disease, which includes administering the anti-fibrosis composition to a subject requiring treatment.

Advantageous Effects

According to the present invention, a peptide comprising an amino acid sequence of SEQ. ID. NO: 1, a peptide having 80% or higher sequence homology with the amino acid sequence or a fragment thereof, a composition including the same, and a method of using the same have an excellent anti-fibrosis effect without side effects. Therefore, tissue fibrosis caused by a TGF-β signaling process, particularly, fibrosis caused by cancer tissue or fibrosis caused by anti-cancer agents or exposure to radiation accompanied by anticancer treatment, etc. can be effectively inhibited and is very useful in preventing and/or treating a fibrotic disease.

DETAILED DESCRIPTION OF THE DRAWINGS/FIGURES

FIG. 1A is a diagram illustrating the entire experiment process of preparing xenograft models, in which nude mice are inoculated with AsPCI cells and then PEP1 and gemcitabine are administered to the mice, starting 10 days later and FIG. 1B is a diagram showing days of administration of PEP1 and/or gemcitabine.

FIG. 2 is a graph showing a weight of each mouse of a control in which nude mice inoculated with AsPC1 cells are not treated with anything, of groups in which each of PEP1 and gemcitabine is administered to nude mice inoculated with AsPC1 cells starting 10 days after inoculation, and of a group in which a combination of PEP1 and gemcitabine is administered to nude mice inoculated with AsPC1 cells from 10 days after inoculation to 24 days after administration to detect in vivo anti-cancer effects of PEP1 and gemcitabine.

Figure 7:
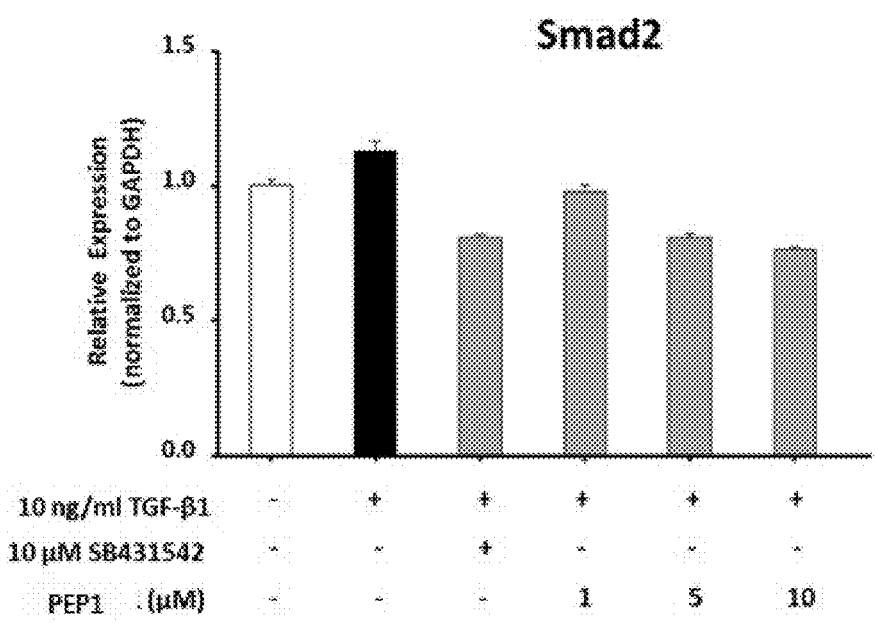

FIG. 7 is a graph showing relative Sma2 expression, which is assessed by qRT-PCR, in a control in which a HepG2 cell line is not treated with anything and an experiment group in which a HepG2 cell line is not treated with anything after TGF-β1 treatment, a positive control in which SB431542 is administered into a HepG2 cell line, and experiment groups in which PEP1 is administered into HepG2 cell lines at different concentrations (1, 5 and 10 μM).

Figure 8:
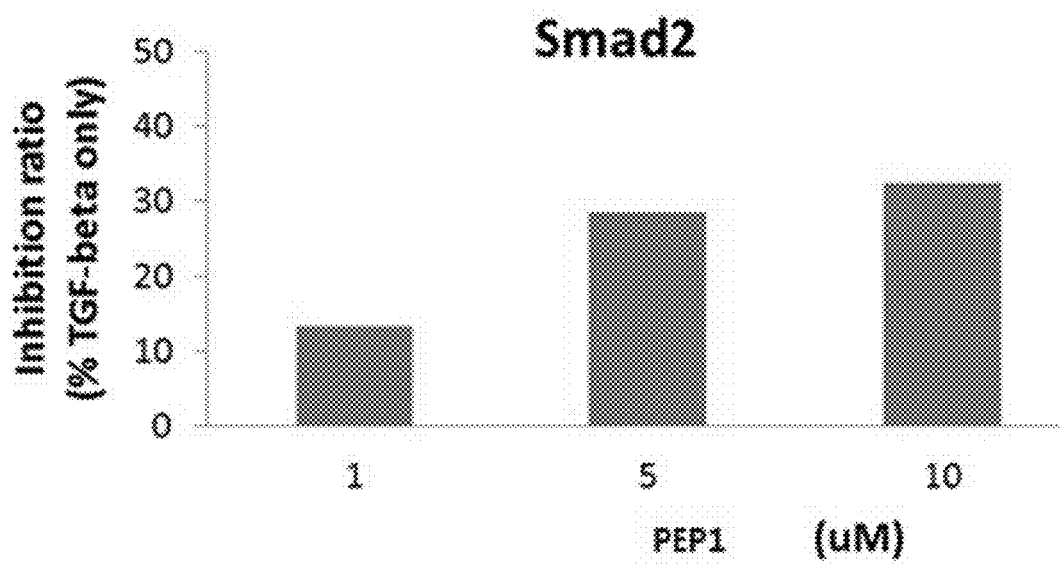

FIG. 8 is a graph showing Smad2 inhibition ratios (%) in each experiment group in which HepG2 cell lines are treated with TGF-β1 and then treated with PEP1 at different concentrations (1, 5 and 10 μM).

Figure 9:
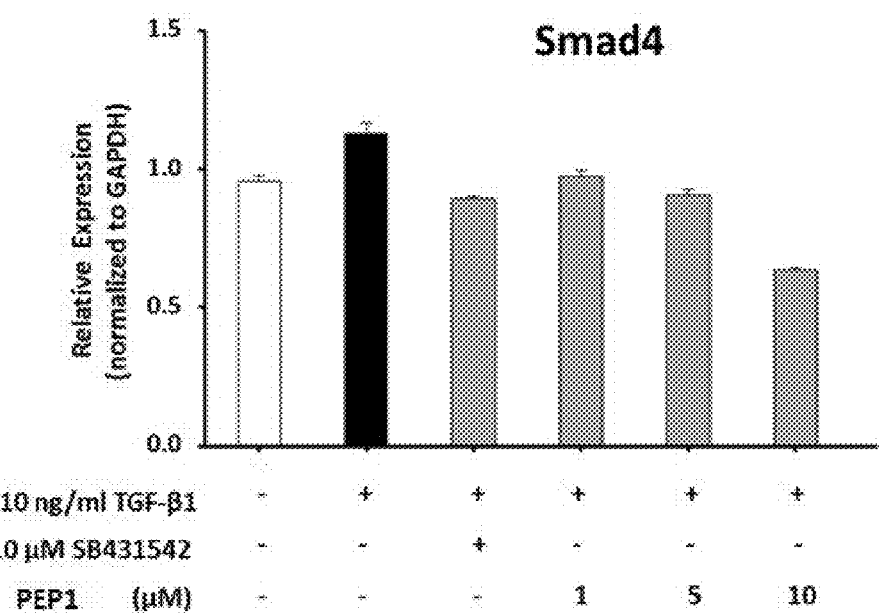

FIG. 9 is a graph showing relative Smad4 expression, which is assessed by qRT-PCR, in a control in which a HepG2 cell line is not treated with anything and an experiment group in which a HepG2 cell line is not treated with anything after TGF-β1 treatment, a positive control in which SB431542 is administered into a HepG2 cell line, and experiment groups in which PEP1 is administered into HepG2 cell lines at different concentrations (1, 5 and 10 μM).

Figure 10:
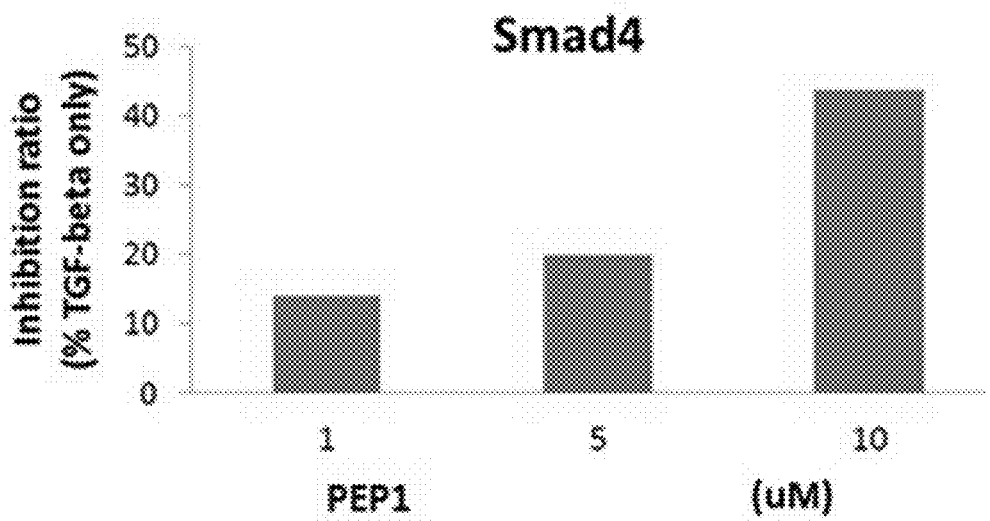

FIG. 10 is a graph showing Smad4 inhibition ratios (%) in experiment groups in which PEP1 is administered into HepG2 cell lines at different concentrations (1, 5 and 10 μM), after TGF-β1 treatment.

Figure 11:
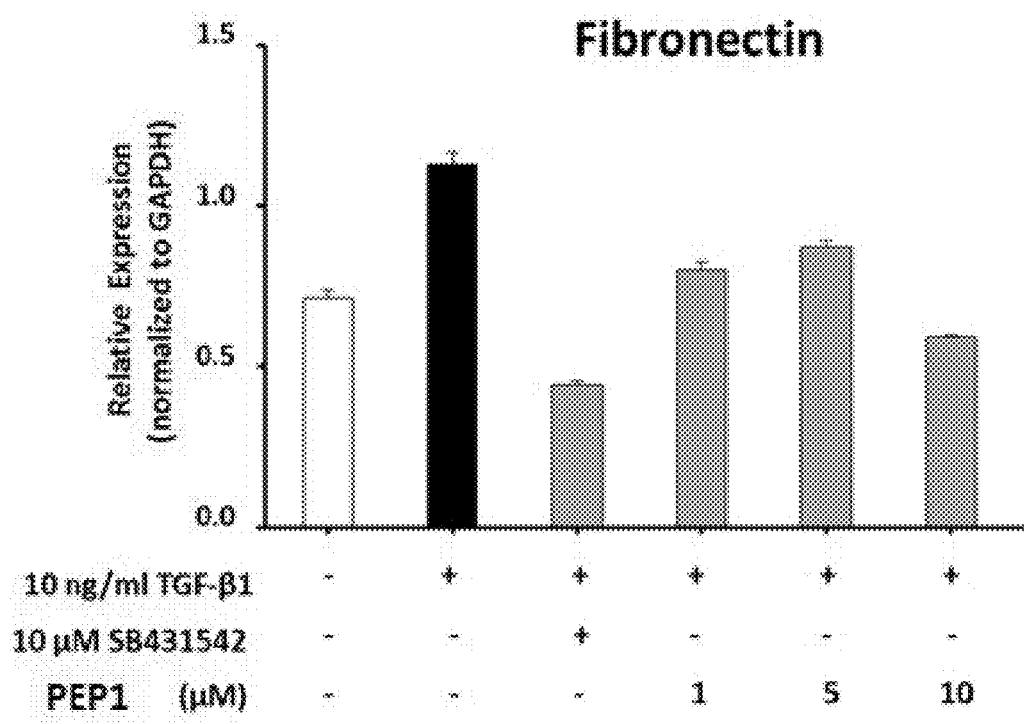

FIG. 11 is a graph showing relative fibronectin expression, which is assessed by qRT-PCR, in a control in which a HepG2 cell line is not treated with anything and an experiment group in which a HepG2 cell line is not treated with anything after TGF-β1 treatment, a positive control in which SB431542 is administered to a HepG2 cell line, and experiment groups in which PEP1 is administered to HepG2 cell lines at different concentrations (1, 5 and 10 μM).

Figure 12:
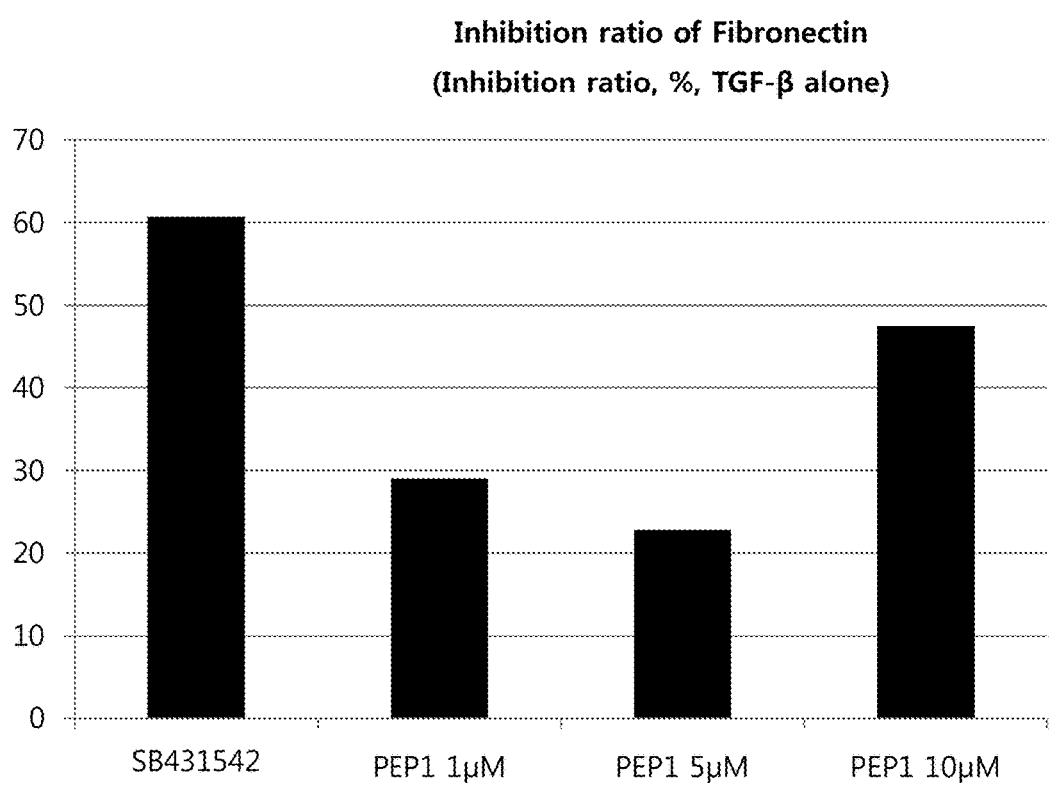

FIG. 12 is a graph showing fibronectin inhibition ratios (%) in a positive control in which HepG2 cell lines are treated with SB431542 and experiment groups in which PEP1 is administered to HepG2 cell lines at different concentrations (1, 5 and 10 μM), after TGF-β1 treatment.

Figure 13:
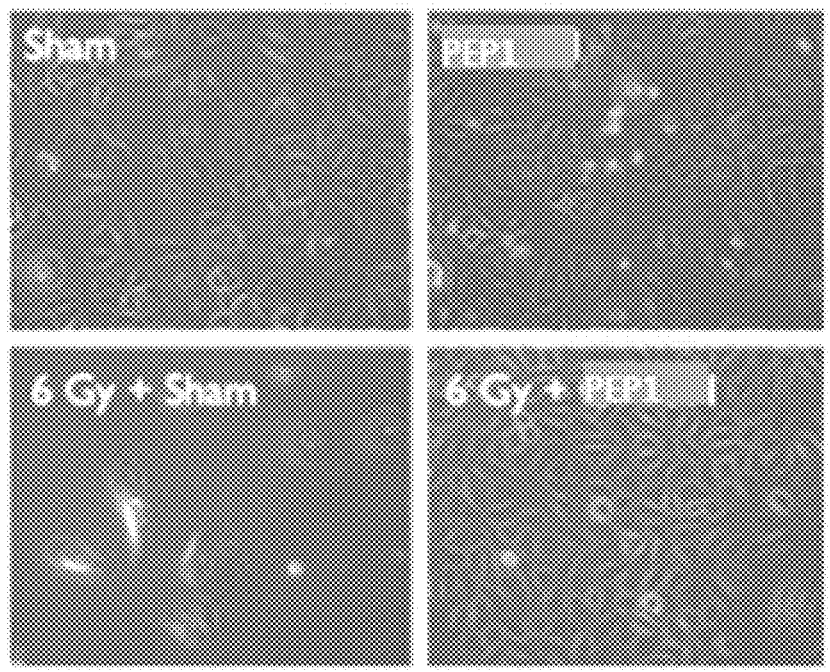

FIG. 13 shows cell culture states in controls in which normal human epidermal keratinocytes (NHEKs) are treated with a placebo (sham) and experimental groups treated with 1 mM of PEP1 10 days after one in each group is exposed to radiation (6 Gy, ionizing radiation (IR)) and the other one in each group is not exposed.

Figure 14:
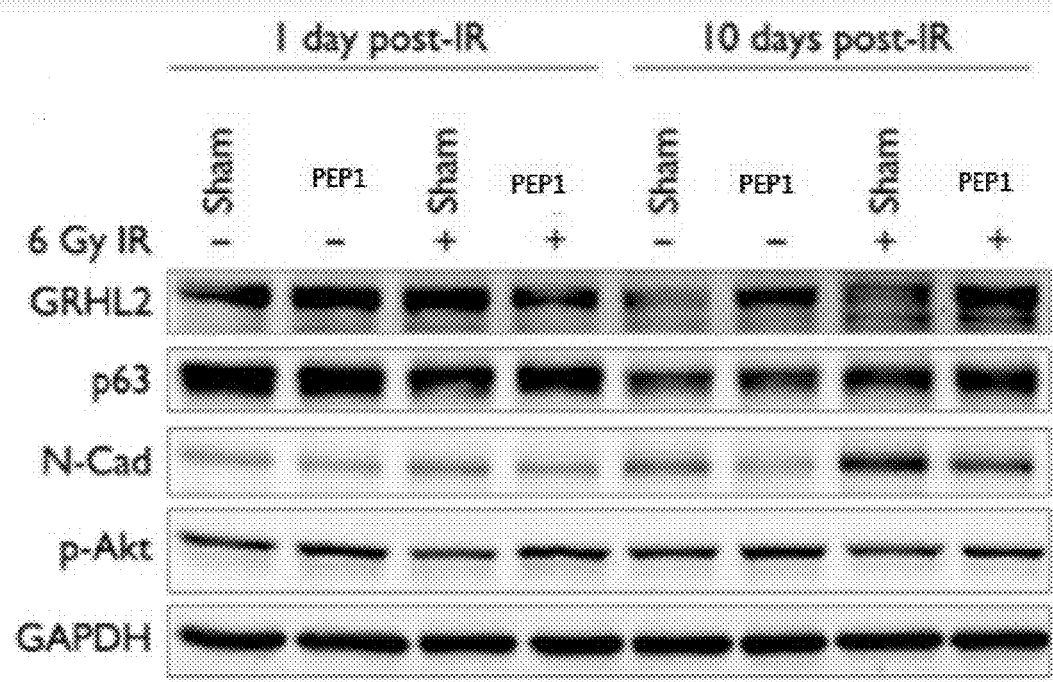

FIG. 14 is electrophoresis images showing GRHL2, p63, N-Cad, and P-Akt expressions in cells of controls in which NHEKs are treated with a placebo (sham) and experiment groups treated with 1 mM of PEP1 one day and 10 days after one in each group is exposed to radiation (6 Gy, ionizing radiation (IR)) and the other one in each group is not exposed.

Figure 15:
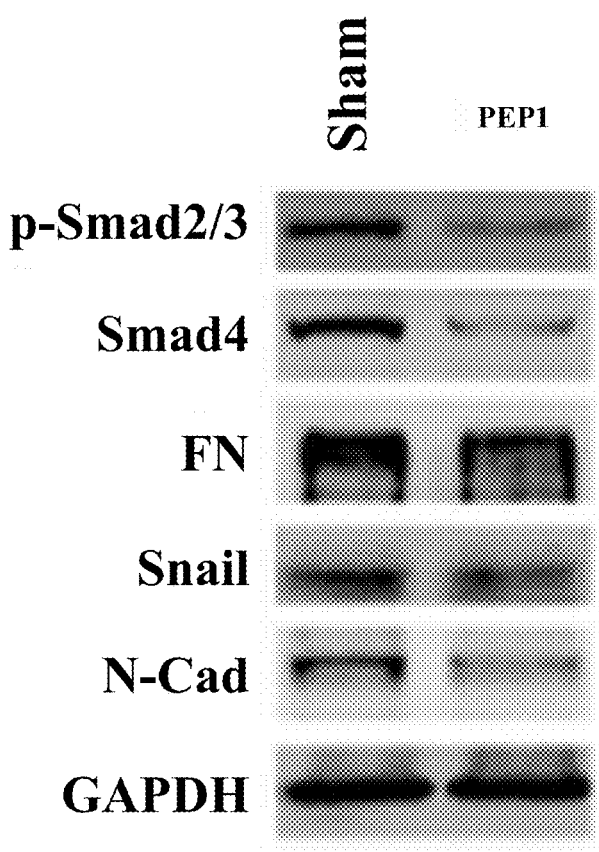

FIG. 15 is western blotting images showing p-Smad2/3, Smad4, FN, Snail and N-Cad expressions in cells of a control in which NHEKs are treated with a placebo (sham) and an experiment group treated with 1 mM of PEP1 after being exposed to radiation (6 Gy, IR).

MODES OF THE INVENTION

Hereinafter, the present invention will be described in further detail with reference to exemplary embodiments. However, the present invention is not limited to specific disclosures, and it should be understood that the present invention includes all modifications, equivalents, and alternatives included in the technical idea and scope of the present invention. For explaining the present invention, the detailed descriptions on related technology known in the art will be omitted when it is determined that they might obscure the gist of the present invention.

Telomere, which is a repetitive genetic material located at each terminus of a chromosome, is known to prevent damage to a corresponding chromosome or coupling to a different chromosome. The telomere is gradually shortened with cell divisions, becoming very short after a certain number of cell divisions, and the cell eventually stops being divided and dies. On the other hand, the elongation of telomeres is known to extend the life span of a cell. As an example, it has been known that, in cancer cells, an enzyme called telomerase is secreted to prevent the shortening of telomeres, resulting in steady proliferation of the cancer cells, without death. The inventors identified that a peptide derived from telomerase is effective in inhibiting fibrosis and thus completed the present invention.

In one aspect of the present invention, a peptide of SEQ. ID. NO: 1, a fragment thereof, or a peptide having 80% or higher sequence homology with the peptide sequence includes telomerase, particularly, a peptide derived from Homo sapiens telomerase.

The peptide disclosed in the specification may include a peptide having 80% or higher, 85% or higher, 90% or higher, 95% or higher, 96% or higher, 97% or higher, 98% or higher, or 99% or higher sequence homology. Also, the peptide disclosed in the specification may include a peptide of SEQ. ID. NO: 1, a fragment thereof, and a peptide in which at least one, two, three, four, five, six, or seven amino acids are modified.

In one aspect of the present invention, some amino acids in a peptide that makes physicochemical characteristics of the peptide of SEQ. ID. NO: 1 changed may be modified within the scope of the present invention. For example, amino acids may be modified to allow the peptide to have enhanced thermal stability, changed substrate specificity, and shifted optimal pH.

The term "amino acid" used herein includes not only the 22 standard amino acids that are naturally integrated into peptide but also the D-isomers and transformed amino acids. Therefore, in one aspect of the present invention, a peptide herein includes a peptide having D-amino acids. On the other hand, in another aspect of the present invention, a peptide may include non-standard amino acids such as those that have been post-translationally modified. Examples of post-translational modification include phosphorylation, glycosylation, acylation (including acetylation, myristorylation, and palmitoylation), alkylation, carboxylation, hydroxylation, glycation, biotinylation, ubiquitinylation, a transformation of chemical properties (e.g. β-removing deimidation, deamidation), and a structural transformation (e.g. formation of a disulfide bridge). The post-translational modification also include changes of amino acids occurring due to chemical reactions when coupling with crosslinkers to form a peptide conjugate, for example, a change of an amino acid occurring at an amino group, a carboxyl group or a side chain.

The peptide disclosed herein may be a wild-type peptide identified and isolated from a natural source. Meanwhile, the peptide disclosed in the specification may be an artificial variant comprising an amino acid sequence in which one or more amino acids are substituted, deleted, and/or inserted, compared with the fragments of the peptide of SEQ. ID. NO: 1. The changing of amino acids in the wild-type polypeptide, as well as the artificial variant, includes the substitution of conservative amino acids, which does not have a significant influence on folding and/or activity of a protein. The conservative substitution may be carried out in the range of the group consisting of basic amino acids (arginine, lysine and histidine), acidic amino acid (glutamic acid and aspartic acid), polar amino acids (glutamine and asparagine), hydrophobic amino acids (leucine, isoleucine, valine and methionine), aromatic amino acids (phenylalanine, tryptophan and tyrosine), and small amino acids (glycine, alanine, serine and threonine). Generally, amino acid substitution that does not change a specific activity is known in the art. The most frequently-occurring exchange takes place between Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly, and vice versa. Other examples of the conservative substitution are shown in Table 1 below.

TABLE 1

| Original amino acid | Exemplary residue substitution | Preferred residue substitution |
| --- | --- | --- |
| Ala (A) | val; leu; ile | Val |
| Arg (R) | lys; gln; asn | Lys |
| Asn (N) | gln; his; asp, lys; arg | Gln |
| Asp (D) | glu; asn | Glu |
| Cys (C) | ser; ala | Ser |
| Gln (Q) | asn; glu | Asn |
| Glu (E) | asp; gln | Asp |
| Gly (G) | Ala | Ala |
| His (H) | asn; gln; lys; arg | Arg |
| Ile (I) | leu; val; met; ala; phe; norleucine | Leu |
| Leu (L) | norleucine; ile; val; met; ala; phe | Ile |
| Lys (K) | arg; gln; asn | Arg |
| Met (M) | leu; phe; ile | Leu |

TABLE 1-continued

| Original amino acid | Exemplary residue substitution | Preferred residue substitution |
| --- | --- | --- |
| Phe (F) | leu; val; ile; ala; tyr | Tyr |
| Pro (P) | Ala | Ala |
| Ser (S) | thr | Thr |
| Thr (T) | Ser | Ser |
| Trp (W) | tyr; phe | Tyr |
| Tyr (Y) | trp; phe; thr; ser | Phe |
| Val (V) | ile; leu; met; phe; ala; norleucine | Leu |

In terms of biological properties of the peptide, a substantial modification is performed by selecting a substitution part which has a considerably different effect in (a) maintaining the backbone structure, for example, a sheet- or helix-like three-dimensional structure, of the polypeptide in a substituted region, (b) maintaining charge or hydrophobicity of the molecule at a target site, or (c) maintaining the bulk of a side chain. Natural residues are classified into the following groups, based on general properties of the side chain:

(1) Hydrophobic: norleucine, met, ala, val, leu, ile;
(2) Neutral hydrophilic: cys, ser, thr;
(3) Acidic: asp, glu;
(4) Basic: asn, gln, his, lys, arg;
(5) Residues affecting chain conformation: gly, pro; and
(6) Aromatic: trp, tyr, phe.

Non-conservative substitutions may be performed by exchanging a member of one of the groups to that of another group. Any cysteine residue, which is not associated with maintaining the proper three-dimensional structure of the peptide, may typically be substituted into serine, thus increasing the oxidative stability of the molecule and preventing improper crosslinks, and, conversely, enhanced stability can be achieved by adding cysteine bond(s) to the peptide.

A different type of amino acid variant of the peptide is made by changing a glycosylation pattern of an antibody. The term "change" used herein refers to deletion of one or more carbohydrate residues that are found on the peptide and/or addition of one or more glycosylation sites which do not exist in the peptide.

Glycosylation in peptides are typically N- or O-linked glycosylation. The term "N-linked glycosylation" used herein refers to attachment of carbohydrate residues to side chains of asparagine residues. As tripeptide sequences, asparagine-X-serine and asparagine-X-threonine (where the X is any amino acid, excluding proline) are recognition sequences for enzymatically attaching a carbohydrate residue to a side chain of an asparagine. Therefore, when one of these tripeptide sequences is present in a polypeptide, a potential glycosylation site is created. The "O-linked glycosylation" used herein refers to the attachment of one of the saccharides, for example, N-acetylgalactosamine, galactose, or xylose, to hydroxyamino acids and, most typically, to serine or threonine, but 5-hydroxyproline or 5-hydroxylysine may also be used.

Addition of a glycosylation site to the peptide is conveniently performed by changing the amino acid sequence to contain the tripeptide sequence described above (for an N-linked glycosylation site). Such a change may be made by addition of one or more serine or threonine residues to the first antibody sequence or by substitution into one of these residues (for an O-linked glycosylation site).

Also, the peptide comprising the sequence of SEQ. ID. NO: 1 or a fragment thereof, or a peptide having 80% or higher sequence homology with the peptide sequence according to one aspect of the present invention has low cytotoxicity and high in vivo stability. In the present invention, SEQ. ID. NO: 1 represents the telomerase-derived peptide, which consists of 16 amino acids as follows.

The peptide set forth in SEQ. ID. NO: 1 is shown in Table 2. The "name" in the Table 2 below is given to distinguish one peptide from another. In one aspect of the present invention, the peptide set forth in SEQ. ID. NO: 1 represents the whole peptide of human telomerase. In another aspect of the present invention, the peptide comprising the sequence of SEQ. ID. NO: 1 or a fragment thereof, or a peptide having 80% or higher sequence homology with the peptide sequence includes a "synthetic peptide" synthesized from a peptide present at a corresponding location that has been selected from the peptides included in telomerase. SEQ. ID. NO: 2 represents the full-length amino acid sequence of the telomerase.

TABLE 2

| SEQ. ID. NO: | Name | Position on telomerase | Sequence | Length |
| --- | --- | --- | --- | --- |
| 1 | pep1 | [611-626] | EARPALLTSRLRFIPK | 16 aa |
| 2 | | [1-1132] | MPRAPRCRAVRSLLRSHYREVLPLATFVRRLGPQGWR LVQRGDPAAFRALVAQCLVCVPWDARPPPAAPSFRQV SCLKELVARVLQRLCERGAKNVLAFGFALLDGARGGP PEAFTTSVRSYLPNTVTDALRGSGAWGLLLRRVGDDV LVHLLARCALFVLVAPSCAYQVCGPPLYQLGAATQAR PPPHASGPRRRLGCERAWNHSVREAGVPLGLPAPGAR RRGGSASRSLPLPKRPRR GAAPEPERTPVGQGSWAHPGRTRGPSDRGFCVVSPAR PAEEATSLEGALSTRHSHPSVGRQHHAGPPSTSRPPR PWDTPCPPVYAETKHFLYSSGDKEQLRPSFLLSSLRPSL TGARRLVETIFLGSRPWMPGTPRRLPRLPQRYWQMRP LFLELLGNHAQCPYGVLLKTHCPLRAAVTPAAGVCAR EKPQGSVAAPEEEDTDPRRLVQLLRQHSSPWQVYGFV RACLRRLVPPGLWGSRHNERRFLRNTKKFISLGKHAK LSLQELTWKMSVRDCAWLRRSPGVGCVPAAEHRLRE EILAKFLHWLMSVYVVELLRSFFYVTETTFQKNRLFFY RKSVWSKLQSIGIRQHLKRVQLRELSEAEVRQHREARP ALLTSRLRFIPKPDGLRPIVNMDYVVGARTFRREKRAE RLTSRVKALFSVLNYERARRPGLLGASVLGLDDIHRA WRTFVLRVRAQDPPPELYFVKVDVTGAYDTIPQDRLT | 1132 aa |

TABLE 2-continued

| SEQ. ID. NO: | Name | Position on telomerase | Sequence | Length |
|---|---|---|---|---|
| | | | EVIASIIKPQNTYCVRRYAVVQKAAHGHVRKAFKSHV STLTDLQPYMRQFVAHLQETSPLRDAVVIEQSSSLNEA SSGLFDVFLRFMCHHAVRIRGKSYVQCQGIPQGSILSTL LCSLCYGDMENKLFAGIRRDGLLLRLVDDFLLVTPHLT HAKTFLRTLVRGVPEYGCVVNLRKTVVNFPVEDEALG GTAFVQMPAHGLFPWCGLLLDTRTLEVQSDYSSYART SIRASLTFNRGFKAGRNMRRKLFGVLRLKCHSLFLDLQ VNSLQTVCTNIYKILLLQAYRFHACVLQLPFHQQVWK NPTFFLRVISDTASLCYSILKAKNAGMSLGAKGAAGPL PSEAVQWLCHQAFLLKLTRHRVTYVPLLGSLRTAQTQ LSRKLPGTTLTALEAAANPALPSDFKTILD | |

In one aspect, the present invention provides a pharmaceutical composition, which includes a peptide with an anti-fibrosis effect, for example, a peptide comprising an amino acid sequence of SEQ. ID. NO: 1, a peptide having 80% or higher sequence homology with the amino acid sequence or a fragment thereof, as an active ingredient.

The anti-fibrosis pharmaceutical composition according to an aspect of the present invention may include a peptide comprising an amino acid sequence of SEQ. ID. NO: 1, a peptide having 80% or more sequence homology with the amino acid sequence or a fragment thereof at a content of 0.01 mg/kg to 0.1 mg/kg, 1 mg/kg, or 10 mg/kg, and when there is a difference in effect according to content, the content may be suitably adjusted. When the composition includes the peptide in the above range or a smaller range, it is suitable for exhibiting an effect intended by the present invention and is able to satisfy both stability and safety requirements of the composition. Moreover, the above range may be appropriate in terms of cost-effectiveness.

In one aspect, the present invention provides a use of a peptide comprising an amino acid sequence of SEQ. ID. NO: 1, a peptide having 80% or higher sequence homology with the amino acid sequence or a fragment thereof to prepare any one of the compositions for inhibiting fibrosis described above.

The composition according to an aspect of the present invention may be applied to all types of animals including humans, dogs, chickens, pigs, cows, sheep, guinea pigs, and monkeys.

In one aspect of the present invention, the composition may be a pharmaceutical composition including a peptide having an anti-fibrosis effect, for example, a peptide comprising an amino acid sequence of SEQ. ID. NO: 1, a peptide having 80% or more sequence homology with the amino acid sequence or a fragment thereof. The pharmaceutical composition according to an aspect of the present invention may be administered orally, rectally, percutaneously, intravenously, intramuscularly, intraperitoneally, intramedullaryly, intrathecally or subcutaneously.

Dosage form for oral administration may be, but not limited to, tablets, pills, soft or hard capsules, granules, a powder, a solution, or an emulsion. Dosage form for parenteral administration may be, but not limited to, injections, drips, lotions, ointments, gels, creams, suspensions, emulsions, a suppository, a patch, or a spray.

The pharmaceutical composition according to one aspect of the present invention, as necessary, may include additives such as diluents, excipients, lubricants, binders, disintegrants, buffers, dispersants, surfactants, coloring agents, flavorings, or sweeteners. The pharmaceutical composition according to one aspect of the present invention may be prepared by a conventional method used in the art.

The active ingredient of the pharmaceutical composition according to one aspect of the present invention may vary according to the patient's age, sex, weight, pathological condition and severity, administration route, or a prescriber's judgment. Administration doses are determined based on these factors by one of ordinary skill in the art, and a daily dose of the pharmaceutical composition may be, for example, 0.1 µg/kg/day to 1 g/kg/day, specifically, 1 µg/kg/day to 100 mg/kg/day, more specifically, 10 µg/kg/day to 10 mg/kg/day, and further more specifically, 50 µg/kg/day to 1 mg/kg/day, but when there is a difference in effect according to dose, the dose may be suitably adjusted. The pharmaceutical composition according to one aspect of the present invention may be administered once to three times a day, but the present invention is not limited thereto.

In one aspect of the present invention, the composition may be an anti-fibrosis composition, which includes a peptide comprising an amino acid sequence of SEQ. ID. NO: 1, a peptide having 80% or more sequence homology with the amino acid sequence, or a fragment thereof, as an active ingredient.

In one aspect of the present invention, the composition may be a composition for inhibiting fibrosis, which is caused by cancer tissue, particularly, pancreatic cancer, stomach cancer, renal cell carcinoma, prostate cancer, larynx cancer, esophageal cancer, thyroid cancer, lung cancer, breast cancer, large and small intestine cancer, uterine cancer, cervical cancer, cancer of uterine body, urinary bladder cancer, genitourinary cancer, bladder cancer, and skin cancer tissue.

The composition according to one aspect of the present invention may be prepared in the form of a tablet, a granule, a powder, a liquid, or a solid. For each form, ingredients, other than an active ingredient, that are conventionally used in the corresponding field, may be easily mixed depending on the form or the purpose of use by one of ordinary skill in the art and may have a synergistic effect when simultaneously applied with a different base material.

Administration doses of the active ingredient are determined by one of ordinary skill in the art, a daily dose of the pharmaceutical composition may be, for example, specifically 1 µg/kg/day to 100 mg/kg/day, more specifically 10 µg/kg/day to 10 mg/kg/day, and further more specifically 50 µg/kg/day to 1 mg/kg/day, and, when there is a difference in effect according to a content, the dose may be suitably adjusted and may vary depending on various factors including a subject's age, health condition, complications, etc.

The terms used in the specification are used only to explain specific examples and not to limit the present invention. Nouns without a number in front thereof do not limit quantity and indicate that at least one article describe by the noun exists. The terms "include", "have" and "contain" are construed as open terms (that is, means that "includes but is not limited").

The mention of a value range is simply because it is an easy way to substitute an alternative to each value included in the range. Unless particularly disclosed otherwise, each value is incorporated herein as if it is individually referred to the specification. End values in all ranges are included in each of the ranges and can be independently combined.

All of the methods mentioned herein may be performed in suitable order unless disclosed otherwise or clearly contradicted by the context. The use of any or all of the embodiments or exemplary language (e.g., "such as") is not only to describe better the present invention, but also to limit the scope of the present invention. No language in the specification should be construed indicating that a non-claimed component is essential for implementation of the present invention. Unless defined otherwise, a technical or scientific term used herein has the same meaning as that usually understood by one of ordinary skill in the art.

Exemplary embodiments of the present invention include the best mode known to the inventors in order to implement the present invention. Variations of the exemplary embodiments may be clearly understood by those of ordinary skill in the art by reading the above descriptions. The inventors expect those of ordinary skill in the art to suitably utilize such variations, and further expect that the present invention is implemented in modes that are different from that described in the specification. Accordingly, the present invention includes, as permitted by the patent law, equivalents and all modifications of the gist of the invention mentioned in the accompanying claims. Moreover, all combinations of the components mentioned in all possible variations are included in the present invention unless disclosed otherwise or is clearly contradictory to the context. The present invention is described in detail with reference to exemplary embodiments, but it will be well understood by those of ordinary skill in the art that the present invention may be changed variously in forms and details without departing from the spirit and scope of the present invention as defined by the following claims.

Hereinafter, the configuration and effect of the present invention will be described in further detail with reference to examples and experimental examples. While the examples and experimental examples below are merely provided to help in understanding the present invention, the category and scope of the present invention are not limited thereto.

Modes of the Invention

Example 1: Synthesis of Peptides

1. Synthesis of Peptides

A peptide of SEQ. ID. NO: 1 (hereinafter, referred to as "PEP1") was prepared according to conventionally known solid peptide synthesis. Specifically, peptides were synthesized by coupling amino acids one by one from the C-terminus through a Fmoc solid phase peptide synthesis (SPPS) using ASP48S (Peptron, Inc., Daejeon, Korea). Resins to which the first amino acid at the C-terminus of peptides is attached, which were used herein, are as follows:

NH$_2$-Lys(Boc)-2-chloro-Trityl Resin
NH$_2$-Ala-2-chloro-Trityl Resin
NH$_2$-Arg(Pbf)-2-chloro-Trityl Resin In all amino acid components used in the peptide synthesis, the N-terminus was protected by Fmoc, and all residues were protected by Trt, Boc, t-butylester (t-Bu), or 2,2,4,6,7-pentamethyl dihydro-benzofuran-5-sulfonyl (Pbf), which were removed from acids. Such amino acid components are as follows:

Fmoc-Ala-OH, Fmoc-Arg(Pbf)-OH, Fmoc-Glu(OtBu)-OH, Fmoc-Pro-OH, Fmoc-Leu-OH, Fmoc-Ile-OH, Fmoc-Phe-OH, Fmoc-Ser(tBu)-OH, Fmoc-Thr(tBu)-OH, Fmoc-Lys(Boc)-OH, Fmoc-Gln(Trt)-OH, Fmoc-Trp(Boc)-OH, Fmoc-Met-OH, Fmoc-Asn(Trt)OH, Fmoc-Tyr(tBu)-OH, Fmoc-Ahx-OH, Trt-Mercaptoacetic acid.

As coupling reagents, 2-(1H-Benzotriazole-1-yl)-1,1,3,3-tetramethylaminium hexafluorophosphate (HBTU)/N-Hydroxybenzotriazole (HOBt)/4-Methylmorpholine (NMM) were used. For Fmoc deprotection, 20% piperidine in DMF was used. For separation from the synthesized peptide from the resin and removal of the protection group of the residue, a cleavage cocktail [TFA (trifluoroacetic acid)/TIS (triisopropylsilane)/EDT (ethanedithiol)/H$_2$O=92.5/2.5/2.5/2.5] was used.

Each peptide was synthesized by repeating a process of protecting corresponding amino acids with an amino acid protection group-coupled start amino acid coupled to a solid phase scaffold, washing with a solvent, and deprotection. After cutting off the synthesized peptide from the resin, the peptide was purified by HPLC, assessed by MS to verify the synthesis, and then lyophilized.

As assessed by high performance liquid chromatography, all peptides used in the example had a purity of 95% or higher.

Detailed procedures for preparing the peptide PEP1 were as follows.

1) Coupling

Protected amino acid (8 equivalents) and coupling agents HBTU (8 equivalents)/HOBt (8 equivalents)/NMM (16 equivalents) dissolved in DMF were added to the NH$_2$-Lys(Boc)-2-chloro-Trityl resin, and the reaction mixture was reacted at room temperature for 2 hours and then sequentially washed with DMF, MeOH, and DMF.

2) Fmoc Deprotection

Following the addition of 20% piperidine in DMF, the reaction mixture was reacted at room temperature for 5 minutes two times, and then sequentially washed with DMF, MeOH, and DMF.

3) The reactions 1 and 2 were repeatedly performed to prepare the basic backbone of a peptide, for example, NH$_2$-E(OtBu)-A-R(Pbf)-P-A-L-L-T(tBu)-S(tBu)-R(Pbf)L-R(Pbf)-F-I-P-K(Boc)-2-chloro-trityl resin.

4) Cleavage: A cleavage cocktail was added to the previously synthesized peptide resin to separate a peptide from the resin.

5) Following the addition of cooling diethyl ether to the obtained mixture, the peptide obtained by centrifugation was precipitated.

6) Following purification by Prep-HPLC, the peptide was analyzed by LC/MS to check molecular weight and lyophilized to obtain a powder.

Example 2: Fibrosis Inhibition by PEP1 in AsPC1 Cell Xenograft Model

To verify in vivo anticancer effects of PEP1 and gemcitabine on pancreatic cancer, xenograft experiments were performed using AsPC1 cell lines. A xenografting method used herein is as follows.

Preparation of Reagents and Materials

Reagents and materials used for the experiment are as follows. After powdery PEP1 was dissolved in 0.2 μm filtered sterile water, aliquots were stored at −70° C. and then dissolved before use, and gemcitabine was dissolved in 100% saline. 5-fluorouracil was dissolved in DMSO.

Preparation of Cell Lines

AsPC1 cell lines (Cell #6×10$^5$ cells/100 ml), which were cell lines used in the experiment, are human pancreatic cancer metastatic cells purchased from the American Type Cell Culture (ATCC, Rockville, Md.). The cell lines were cultured at 37° C. to give a cell density of 1 to 2×10$^6$/ml in Roswell Park Memorial Institute (RPMI 1640) medium containing 10% fetal bovine serum (FBS), 50 U/ml penicillin, and 50 μg/ml streptomycin.

Experimental Methods

AsPC1 cells were injected into each of nude mouse experiment groups ① to ④. The reagents and materials and method of culturing cell lines, which were used in the experiment, are the same as described in Example 1.

Figure 1:
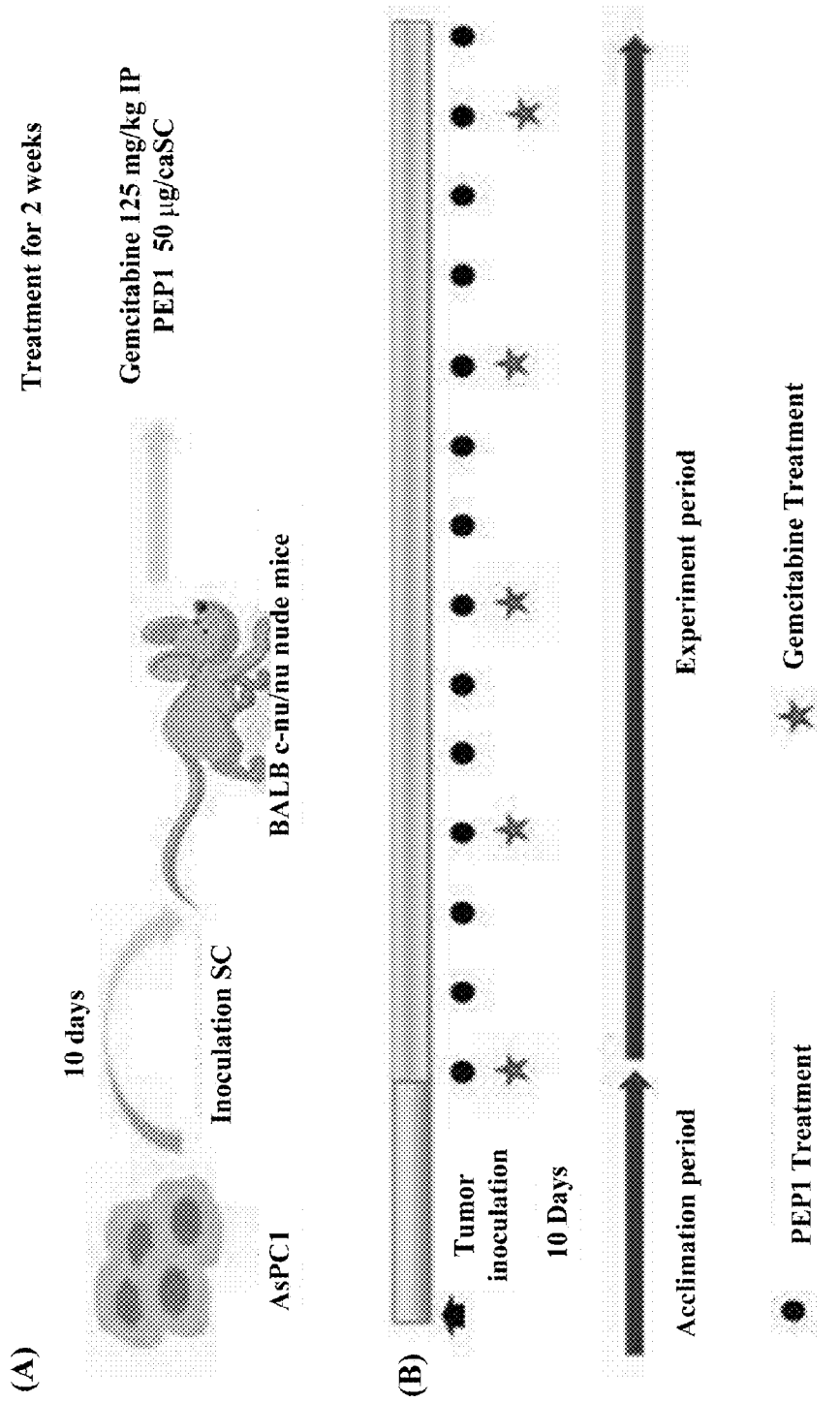

The cultured 5×10$^6$ AsPC1 cells were subcutaneously injected into nude mice (BALB/c-nu/nu nude mice, purchased from Joongang Laboratory animal, Seoul, Korea). The injection was performed until cancer was grown to a size of 100 mm$^3$ (about 10 days). Following cancer engraftment, the mice were divided into groups, each group having a similar average weight, and then either or both of gemcitabine and Pep1 were subcutaneously and intraperitoneally injected into the mice according to the conditions for each of the four experiment groups below (refer to FIG. 1). Cancer volume was measured with calipers and calculated by the following formula [width$^2$×length×0.52].

After grafting, either or both of Pep1 and gemcitabine were administered to each of the four experiment groups.

① AsPC1 grafting control
② AsPC1 grafting+PEP1 2 mg/kg (once a day, s.c) administered group
③ 2 mg/kg grafting+gemcitabine 125 mg/kg (once every third day, i.p) administered group
④ 2 mg/kg grafting+PEP1 2 mg/kg (once a day, s.c)+gemcitabine 125 mg/kg administered group (once every third day, i.p)

After then, weight of each mouse was quantified every time. Also, cancer tissue sample preparation and cell proliferation marker (PCNA)/apoptosis marker (TUNEL) staining were performed.

For analyses of experiment results, averages between several experiment groups was assessed by a student's t-test. The standard of statistical significance was set as p=0.0002.

Experimental Results

Figure 2:
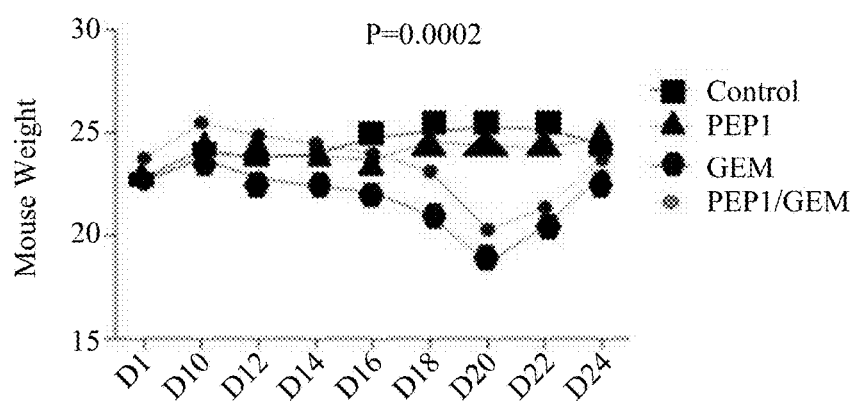

According to the analyses of individual experiment groups, it can be seen that, when a combination of gemcitabine and PEP1, and gemcitabine were administered, the weight of a mouse was the smallest at day 20 after the administration (refer to FIG. 2).

FIGS. 3 to 6 show cells in each experiment group.

Figure 3:
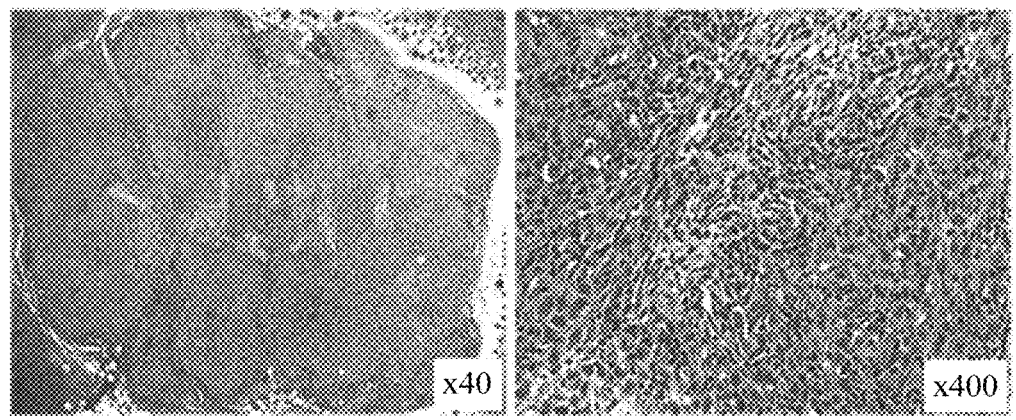
FIG. 3 shows cell images of the control in which the nude mice inoculated with AsPC1 cells are not treated with anything.
Figure 4:
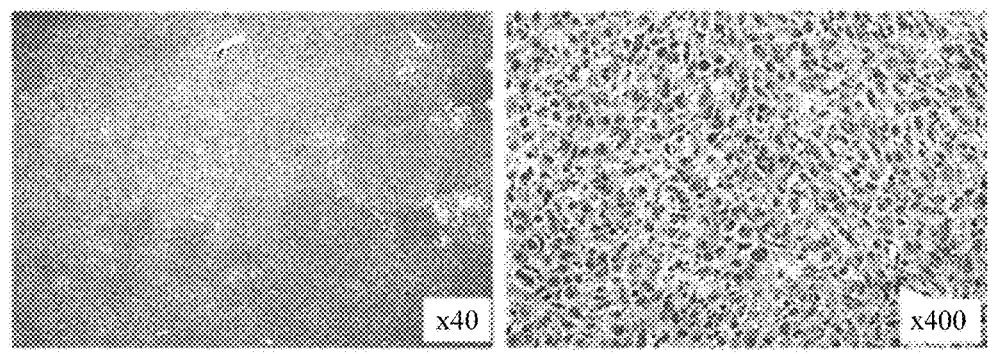
FIG. 4 shows cell images of the group in which PEP1 is subcutaneously administered to the nude mice inoculated with AsPC1 cells once a day, starting 10 days after inoculation.

In the AsPC1 cell-inoculated control (group ①; refer to FIG. 3), it was shown that collagen parts stained in blue color (corresponding to the dark gray parts in FIG. 3) were increased between cancer cells stained in red color (corresponding to the light gray parts in FIG. 3). That is, it can be seen that fibrosis is considerably developed due to cancer.

In group ② in which AsPC1 cells were treated with PEP1 (refer to FIG. 4), compared with FIG. 3, parts stained in blue color (corresponding to the dark gray parts in FIG. 4) were not shown. This indicates that collagen was reduced, and thus, fibrosis was considerably inhibited by PEP1.

Meanwhile, in group ③ in which AsPC1 cells were treated with gemcitabine (refer to FIG. 5), it can be seen that parts stained in red color (corresponding to black parts in FIG. 5) were considerably reduced, and the parts stained in blue color (corresponding to the light gray parts in FIG. 5) were increased. This indicates that cancer cells were killed by gemcitabine, but fibrosis was considerably developed.

Here, remaining red-colored cells may probably be an anticancer agent against CD133+ cancer stem cells. In pancreatic cancer, it was known that the CD133+ cancer stem cells have resistance to gemcitabine, which is an anticancer agent, and development of fibrosis around these cells demonstrates that drug delivery is not well performed.

Figure 5:
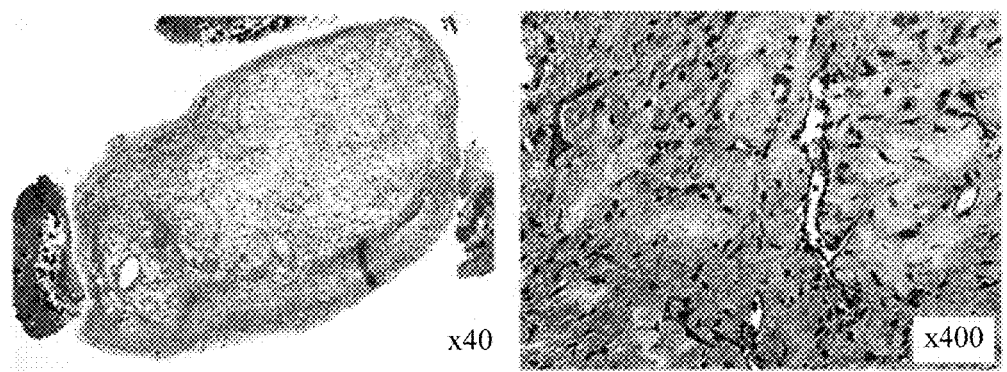
FIG. 5 shows cell images of the group in which gemcitabine is intraperitoneally administered to the nude mice inoculated with AsPC1 cells once every third day, starting 10 days after inoculation.
Figure 6:
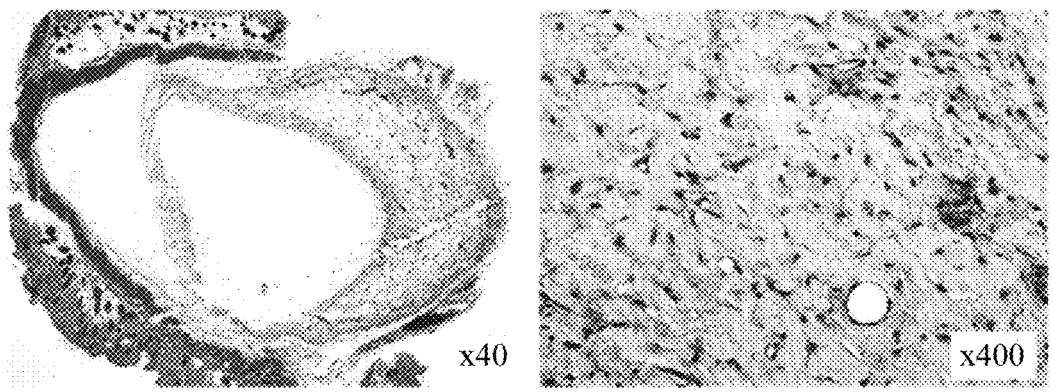
FIG. 6 shows cell images of the group in which both of PEP1 (once a day, subcutaneously) and gemcitabine (once every third day, intraperitoneally) are administered to the nude mice inoculated with AsPC1 cells starting 10 days after inoculation.

However, compared with FIG. 5, in group ④ in which AsPC1 cells were treated with PEP1 and gemcitabine (refer to FIG. 6), it was observed that parts stained in blue color (corresponding to the light gray parts in FIG. 6) were reduced. It was seen that fibrosis was considerably inhibited by PEP1, and thus the inhibition of drug delivery due to fibrosis was considerably reduced, which indicates that intracellular delivery of gemcitabine, which is an anticancer agent, may more easily occur.

Example 3: TGF-β Inhibitory Effect of PEP1 in HepG2 Cell Lines

To verify the TGF-β inhibitory effect of PEP1, which is considered as the main cause of fibrosis, an experiment for confirming a TGF-β signaling inhibiting action in HepG2 cell lines was performed as follows.

Preparation of Reagents and Materials

Reagents and materials used in the experiment are as follows. After powdery PEP1 was dissolved in 0.2 μm filtered sterile water, aliquots were stored at −70° C. and then dissolved before use. As a cell line, HepG2 (ATCC HB-8065; American Type Culture Collection) was used, and recombinant human TGF-β1 was dissolved in 4 mM HCl, thereby preparing a 10 μg/mL stock. SB431542 (Sigma) used as a positive control was prepared in a 10 mM stock.

Preparation of Cell Lines

2×10$^6$ HepG2 cells (ATCC HB-8065) were seeded into a 60 mm petri-dish and cultured in a CO$_2$ incubator for 16 hours. Afterward, media were transferred to serum-free media (SFM), and then the cells were further cultured for 24 hours. Subsequently, 10 ng/ml of TGF-β1 was added to the media, and then various concentrations of PEP1 (0.1, 1, 5, 10 μM) were treated to media, followed by culturing for 72 hours. Each treated group was further cultured in a CO$_2$ incubator for 1 hour at 37° C.

Experiment for Analyzing Expression of TGF-β Inhibition-Related Genes

RNA was extracted from peptide-treated cells using an RNEASY® Plus Mini Kit (Qiagen) (RNA extraction kit) according to the manufacture's protocol. The extracted RNA was quantified, and then cDNA was synthesized from 1 μg of total RNA using a reverse transcription system (Promega). Afterward, qRT-PCR was performed using a CFX96-real-time system (Bio-rad). As TGF-β-related biomarkers, mRNA expression of fibronectin (FN), Smad2 and Smad4 were analyzed, and as a reference gene, GAPDH was used. For PCR, primers of each gene were constructed as follows. The genes were amplified real time using the primers of Table 3 below with 40 cycles (95° C., 15 sec, 57° C., 30 sec, 72° C., 30 sec). The nucleotide sequences of the primers are as follows.

TABLE 3

| Gene | Forward sequence (5'-3') | Reverse sequence (5'-3') |
| --- | --- | --- |
| FN | CAGGATCACTTACGGAGAAACAG (SEQ. ID. NO: 3) | GCCAGTGACAGCATACACAGTG (SEQ. ID. NO: 4) |
| Smad2 | ATCCTAACAGAACTTCCGCC (SEQ. ID. NO: 5) | CTCAGCAAAAACTTCCCCAC (SEQ. ID. NO: 6) |
| Smad4 | GCATCGACAGAGACATACAG (SEQ. ID. NO: 7) | CAACAGTAACAATAGGGCAG (SEQ. ID. NO: 8) |
| GAPDH | AGGGCTGCTTTTAACTCTGGT (SEQ. ID. NO: 9) | CCCCACTTGATTTTGGAGGGA (SEQ. ID. NO: 10) |

Experiment Results

The TGF-β inhibitory effects of PEP1 were evaluated by qRT-PCR. Following 48-hour culture of PEP1 in the presence of TGF-β, mRNA expression levels of TGF-β-related genes such as Smad2 and Smad4 were measured and compared with the reference gene GAPDH (refer to FIGS. 7, 8, 9 and 10). Compared with the non-treated control, Smad2 and Smad4 expression was increased in the TGF-β treated group, and in the positive control SB431542, compared with the TGF-β treated group, as the concentration of PEP1 was increased, the Smad2 and Smad4, as TGF-β biomarkers, were concentration-dependently inhibited.

Also, decreased expression of fibronectin, which is a TGF-β-related fibrosis gene, shown after 48-hour culture of PEP1 in the presence of TGF-β was assessed by comparing mRNA expression levels of fibronectin and GAPDH (refer to FIG. 11). Compared with the non-treated negative control, in the TGF-β treated group, fibronectin expression was increased. Meanwhile, in the positive control SB431542, compared with the TGF-β treated group, the PEP1 treated group showed fibronectin inhibition as the concentration of PEP1 was increased. The positive control (SB431542) showed an inhibition ratio of 60.7%, and PEP1 showed an inhibition ratio of 22.8% to 47.5% (refer to FIG. 12).

Such results can show that PEP1 has a direct effect of inhibiting the expression of Smad2 and Smad4, which are downstream genes involved in the TGF-β signaling mechanism, and inhibits the fibronectin expression induced by TGF-β and thus has a possibility as an agent for preventing and treating fibrosis.

Example 4: TGF-4 Inhibitory Effect of PEP1 in Radiation-Exposed NHEK Cell Lines

To confirm PEP1 effects on fibrosis induced by radiation exposure for anticancer treatment and other tumor treatments, an experiment for confirming a TGF-β inhibitory effect of PEP1 in radiation-exposed NHEKs was performed.
Preparation of Reagents and Cell Lines PEP1 synthesized according to Example 1 and a placebo (sham) as a control were prepared. Normal human epidermal keratinocytes (NHEKs) were cultured in a monolayer to be used for a radiation exposure experiment. For the radiation exposure experiment, ionized radiation was used at an intensity of 6 Gy.
Experiment Method To examine the cell differentiation of NHEK cell lines according to radiation exposure, NHEKs were treated with each of the placebo and 1 mM of PEP1, and then divided into radiation-exposed groups and non-exposed groups, followed by culturing for 10 days (refer to FIG. 13).

Also, to examine the change in expression levels of biomarkers for the NHEK cell lines due to the radiation exposure, the NHEKs were treated with each of the placebo and 1 mM of PEP1 and divided into non-exposed groups (−) and radiation-exposed groups (+), and then expression levels of the biomarkers were examined at day 1 and day 10 after the radiation exposure (refer to FIG. 14). In measurement of the expression levels of the biomarkers, GAPDH was used as a reference control.

In addition, to exactly observe the inhibition of TGF-β signaling by PEP1 when the NHEKs were continuously cultured after the radiation exposure, the cells were divided into a group in which the radiation (6 Gy, IR)-exposed NHEKs were treated with a placebo (sham) and a 1 μM PEP1-treated group and then cultured for 10 days. The expression levels of respective markers were observed by performing western blotting on the TGF-β and fibrosis-related biomarkers (refer to FIG. 15).

Western blotting procedures were as follows. Peptide-treated cells were washed with PBS twice, collected into a 1.5 mL centrifuge tube using a cell scraper, followed by centrifugation (1,000 rpm, 4° C., 2 minutes). After removal of the obtained supernatant, 100 μL of RIPA buffer was added to the NHEKs. The cells were cultured on ice for 40 minutes and vortexed every 10 minutes (micro-centrifuge was previously cooled at 4° C.), and then the sample was stirred using a 1 ml syringe 40 to 50 times. Finally, the sample was centrifuged at 13,000 rpm for 15 minutes to obtain a supernatant.

30 g of protein was transferred to a PVDF membrane (Millipore) by 8% sodium dodecyl sulfate-polyacrylamide gel electrophoresis (SDS-PAGE). The PVDF membrane was blocked with 5% skim milk, and incubated with specific primary antibodies. The antibodies used in the experiment were as follows: fibronectin (285 kDa, 5% BSA 1:3000, ab2413, Abcam), N-Cadherin (140 kDa, 5% BSA 1:1000, #4061, Cell Signaling), Smad4 (70 kDa, 5% BSA 1:1000, #9515, Cell Signaling), Smad 2/3 (60, 52 kDa, 5% BSA 1:1000, #3102, Cell Signaling), P-Akt (60 kDa, 5% BSA 1:1000, #9271, Cell Signaling), pSmad 2/3 (Cell Signaling #3102), GRHL2 (Abeam #ab15532), GAPDH (37 kDa, 5% BSA 1:1000, #2118, Cell Signaling). Subsequently, the PVDF membrane was washed with tris-buffered saline containing 0.1% TWEEN® 20 (TBST) and reacted with HRP-conjugated anti-rabbit antibodies (Jackson Immuno Research Laboratories, INC.). Afterward, ECL detection (Amersham Pharmacia Biotech) was performed, and obtained images were analyzed using an image analyzer (GE Healthcare, IMAGEQUANT™ LAS 4000).

Experimental Results

In an experiment of cell differentiation in NHEK cell lines according to radiation exposure, after a radiation exposure, a control showed differentiation (fibrosis development), but the PEP1 treated group hardly showed differentiation even after the radiation exposure. These results show that the progression of fibrosis caused by the radiation exposure may be inhibited by PEP1 administration.

In an experiment for observing changes in expression levels of biomarkers in NHEK cell lines according to radiation exposure, levels of increased expression of biomarkers GRHL2, p63, and N-Cad 10 days after the radiation exposure were observed in each experiment group. This showed that the expression levels of the biomarkers GRHL2 and p63, which had TGF-β signaling inhibitory effects, were decreased in the placebo treated group and increased in the PEP1 treated group. Such results demonstrate that the expression of GRHL2 and p63, which have inhibitory effects on TGF-β signaling involved in fibrosis development after the radiation exposure, were increased by PEP1.

Meanwhile, the expression level of a biomarker N-Cad expressed in fibrotic tissue was increased in the placebo (sham) treated group and decreased in the PEP1 treated group. The expression level of P-Akt (phosphorylation of Akt (protein kinase B)), which is a biomarker indicating a degree of cell survival, was increased in the PEP1 treated group. These results demonstrate that not only can PEP1 inhibit fibrosis development by the radiation exposure, but it can also be involved in a cell survival mechanism.

From the results of the experiment, PEP1 raised the expression of GRHL2 and p63 to inhibit the TGF-β signaling process, and thus fibrosis was able to be inhibited by the TGF-β signaling caused by the radiation exposure. Therefore, it can be seen that PEP1 has a possibility as a drug for preventing or treating fibrosis caused by radiation exposure and fibrosis of tissue cells.

Example 5: Verification of In Vitro and In Vivo Radiation Defensive Effects and Tissue Fibrosis Inhibitory Effects of PEP1

Preparation of Reagents, Cell Lines and Experimental Animals

PEP1 synthesized according to Example 1 and a placebo (sham) used as a control were prepared. NHEKs were cultured in a monolayer to prepare an in vitro radiation exposure experiment. For in vitro, in situ, and in vivo radiation exposure experiments, ionized radiation was used at various intensities ranging from 0 to 10 Gy (0, 2, 4, 6, 8, and 10 Gy).

Meanwhile, experimental animals were divided into two animal models. The first model was an oral mucositis model, which was prepared by inducing an ulcer to the tongue of each C3H mouse by exposing the head and the neck to radiation (6 Gy, IR) for 5 straight days. The second model is a dermal fibrosis model, which was prepared by inducing local scleroderma by subcutaneously injecting 0.1 cc of a dilution of bleomycin which was known as the cause of pulmonary fibrosis in a 0.9% NaCl aqueous solution at a concentration of 0.5 mg/ml once a day for 24 to 28 days.

Experimental Method and Results

In vitro and in situ experiments were performed on NHEK cell lines for confirming a PEP1 defensive effect on radiation exposure damage and showed that, when NHEKs were divided into groups, each treated with a placebo or PEP1 and then exposed to radiation at various intensities ranging from 0 to 10 Gy (0, 2, 4, 6, 8, and 10 Gy), expression levels of a marker exhibiting radiation exposure damage represented by radiation-induced premature senescence (RIPS), a DNA damage response (DDR) protein, and markers for senescence-associated heterochromatin foci (SAHF) were confirmed. The expression level of each marker was measured using qRT-PCR, western blotting, and immunofluorescence staining. For the measurement of the levels, senescence-associated β-galactosidase (SA β-Gal), p16INK4A, p-p53Ser15, p-ATM, γ-H2AX, 53BP1,H3K9me3, HP1γ, and HMGA2 were used as markers.

Meanwhile, to confirm a PEP1 inhibitory effect on tissue fibrosis induced by TGF-β or bleomycin treatment in NHEK cell lines through an in vitro experiment, NHEKs were treated with each of a placebo and PEP1 to give a final concentration of 10 µg/ml, cultured, and treated with TGF-β and bleomycin every 48 hours, followed by measuring expression levels of fibronectin (FN) and collagen type 1 (Col 1α1) using qRT-PCR and western blotting.

For the in vivo experiment, first, in the first oral mucositis model, C3H mice were divided into groups, each intraperitoneally treated with a placebo or PEP1 to give a final dose of 1 mg/kg and exposed to radiation (6 Gy, IR) for five consecutive days to induce a tongue ulcer corresponding to an oral mucositis. Ten days later, the mice were sacrificed to collect tongue tissue, which was stained with toluidine blue and by H&E staining, to perform biopsy. In addition, using a comparative control which was treated with rapamycin for 5 days at a dose of 5 mg/kg per day, an experiment for relatively examining PEP1 effects was performed.

Meanwhile, in the second dermal fibrosis model, C3H mice were divided into groups, each intraperitoneally treated with a placebo or PEP1 to give the final dose of 50 mg/kg, and subcutaneously treated with bleomycin at the concentrations mentioned in the preparation of the experimental animals for 24 to 28 days. 28 days later, the mice were sacrificed to detect scleroderma, followed by an experiment for examining fibrosis diffusion using Masson's trichrome staining.

According to the in vitro and in vivo animal model experiments, it can be seen that the PEP1 treatment exhibits a defensive effect on radiation exposure damage. Specifically, according to the in vitro experiment, it can be seen that the PEP1 has an RIPS inhibitory effect, which was indicated by inhibition of the marker expression, and according to the in vivo experiment, it can be seen that the PEP1 has defensive effects against exposure to radiation and induction of tissue fibrosis, which were indicated by biopsy.

According to the experiment examples, it can be seen that the PEP1 and the composition including the PEP1 according to the present invention have effects of preventing or treating senescence and diseases related to cellular fibrosis occurring in various regions due to various reasons including TGF-β signaling, tissue fibrosis caused by cancer, treatment with an anticancer agent, and radiation exposure. Therefore, it is concluded that a therapeutic agent or a treating method for preventing or treating fibrosis-related senescence and diseases can be developed using PEP1 and a composition including the PEP1 according to the present invention.

What is claimed is:

1. A method of treating a fibrotic disease comprising administering to a subject in need thereof an isolated peptide of SEQ ID NO: 1, wherein the fibrotic disease is induced by cancer or administration of an anticancer agent.

2. The method according to claim 1, wherein the fibrotic disease is fibrosis induced by cancer selected from the group consisting of pancreatic cancer, colorectal cancer, stomach cancer, prostate cancer, non-small cell lung cancer, breast cancer, melanoma, and ovarian cancer.

3. The method according to claim 1, wherein the peptide is administered with a chemotherapeutic agent.

4. The method according to claim 3, wherein the chemotherapeutic agent is at least one selected from the group consisting of deoxynucleoside analogs and fluoropyrimidines.

5. The method according to claim 4, wherein the deoxynucleoside analog is gemcitabine, and the fluoropyrimidine is 5-fluorouracil or capecitabine.

6. The method according to claim 1, wherein the peptide is administered at a daily dose of 0.1 µg/kg to 1 g/kg.

7. A method of treating a fibrotic disease comprising administering to a subject in need thereof a composition comprising an isolated peptide of SEQ ID NO. 1, wherein the fibrotic disease is induced by cancer or administration of an anticancer agent.

8. The method according to claim 7, wherein the fibrotic disease is fibrosis induced by cancer selected from the group consisting of pancreatic cancer, colorectal cancer, stomach cancer, prostate cancer, non-small cell lung cancer, breast cancer, melanoma, and ovarian cancer.

9. The method according to claim 7, wherein the method further comprises administration of a chemotherapeutic agent.

10. The method according to claim 9, wherein the chemotherapeutic agent is at least one selected from the group consisting of deoxynucleoside analogs and fluoropyrimidines.

11. The method according to claim 10, wherein the deoxynucleoside analog is gemcitabine, and the fluoropyrimidine is 5-fluorouracil or capecitabine.

12. The method according to claim 7, wherein the composition is administered at a daily dose of 0.1 µg/kg to 1 g/kg.

13. The method according to claim 7, wherein the composition is administered through oral, rectal, percutaneous, intravenous, intramuscular, intraperitoneal, intramedullar, intrathecal, or subcutaneous routes.

14. The method according to claim 7, wherein the composition further comprises pharmaceutically acceptable excipients and additives.

15. The method according to claim 14, wherein the composition inhibits fibrosis of dermal tissue via transforming growth factor-β (TGF-β) signaling process.

16. The method according to claim 15, wherein the composition is a cosmetic composition.

* * * * *

SEQUENCE LISTING

<160> NUMBER OF SEQ ID NOS: 10

<210> SEQ ID NO 1
<211> LENGTH: 16
<212> TYPE: PRT
<213> ORGANISM: Homo sapiens

<400> SEQUENCE: 1

Glu Ala Arg Pro Ala Leu Leu Thr Ser Arg Leu Arg Phe Ile Pro Lys
1               5                   10                  15

<210> SEQ ID NO 2
<211> LENGTH: 1132
<212> TYPE: PRT
<213> ORGANISM: Homo sapiens

<400> SEQUENCE: 2

Met Pro Arg Ala Pro Arg Cys Arg Ala Val Arg Ser Leu Leu Arg Ser
1               5                   10                  15

His Tyr Arg Glu Val Leu Pro Leu Ala Thr Phe Val Arg Arg Leu Gly
                20                  25                  30

Pro Gln Gly Trp Arg Leu Val Gln Arg Gly Asp Pro Ala Ala Phe Arg
            35                  40                  45

Ala Leu Val Ala Gln Cys Leu Val Cys Val Pro Trp Asp Ala Arg Pro
50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
        115                 120                 125

Asp Ala Leu Arg Gly Ser Gly Ala Trp Gly Leu Leu Leu Arg Arg Val
130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
        195                 200                 205

Glu Ala Gly Val Pro Leu Gly Leu Pro Ala Pro Gly Ala Arg Arg Arg
210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
        275                 280                 285

Leu Ser Gly Thr Arg His Ser His Pro Ser Val Gly Arg Gln His His
290                 295                 300

Ala Gly Pro Pro Ser Thr Ser Arg Pro Pro Arg Pro Trp Asp Thr Pro

```
            305                 310                 315                 320
        Cys Pro Pro Val Ala Glu Thr Lys His Phe Leu Tyr Ser Ser Gly
                        325                 330                 335

Asp Lys Glu Gln Leu Arg Pro Ser Phe Leu Ser Ser Leu Arg Pro
                        340                 345                 350

Ser Leu Thr Gly Ala Arg Arg Leu Val Glu Thr Ile Phe Leu Gly Ser
                        355                 360                 365

Arg Pro Trp Met Pro Gly Thr Pro Arg Leu Pro Arg Leu Pro Gln
                370                 375                 380

Arg Tyr Trp Gln Met Arg Pro Leu Phe Leu Glu Leu Leu Gly Asn His
        385                 390                 395                 400

Ala Gln Cys Pro Tyr Gly Val Leu Leu Lys Thr His Cys Pro Leu Arg
                        405                 410                 415

Ala Ala Val Thr Pro Ala Ala Gly Val Cys Ala Arg Glu Lys Pro Gln
                        420                 425                 430

Gly Ser Val Ala Ala Pro Glu Glu Glu Asp Thr Asp Pro Arg Arg Leu
                        435                 440                 445

Val Gln Leu Leu Arg Gln His Ser Ser Pro Trp Gln Val Tyr Gly Phe
                        450                 455                 460

Val Arg Ala Cys Leu Arg Arg Leu Val Pro Pro Gly Leu Trp Gly Ser
        465                 470                 475                 480

Arg His Asn Glu Arg Arg Phe Leu Arg Asn Thr Lys Lys Phe Ile Ser
                                485                 490                 495

Leu Gly Lys His Ala Lys Leu Ser Leu Gln Glu Leu Thr Trp Lys Met
                        500                 505                 510

Ser Val Arg Asp Cys Ala Trp Leu Arg Arg Ser Pro Gly Val Gly Cys
                        515                 520                 525

Val Pro Ala Ala Glu His Arg Leu Arg Glu Glu Ile Leu Ala Lys Phe
                        530                 535                 540

Leu His Trp Leu Met Ser Val Tyr Val Val Glu Leu Leu Arg Ser Phe
        545                 550                 555                 560

Phe Tyr Val Thr Glu Thr Thr Phe Gln Lys Asn Arg Leu Phe Phe Tyr
                                565                 570                 575

Arg Lys Ser Val Trp Ser Lys Leu Gln Ser Ile Gly Ile Arg Gln His
                        580                 585                 590

Leu Lys Arg Val Gln Leu Arg Glu Leu Ser Glu Ala Glu Val Arg Gln
                        595                 600                 605

His Arg Glu Ala Arg Pro Ala Leu Leu Thr Ser Arg Leu Arg Phe Ile
                610                 615                 620

Pro Lys Pro Asp Gly Leu Arg Pro Ile Val Asn Met Asp Tyr Val Val
        625                 630                 635                 640

Gly Ala Arg Thr Phe Arg Arg Glu Lys Arg Ala Glu Arg Leu Thr Ser
                                645                 650                 655

Arg Val Lys Ala Leu Phe Ser Val Leu Asn Tyr Glu Arg Ala Arg Arg
                        660                 665                 670

Pro Gly Leu Leu Gly Ala Ser Val Leu Gly Leu Asp Asp Ile His Arg
                        675                 680                 685

Ala Trp Arg Thr Phe Val Leu Arg Val Arg Ala Gln Asp Pro Pro Pro
                690                 695                 700

Glu Leu Tyr Phe Val Lys Val Asp Val Thr Gly Ala Tyr Asp Thr Ile
        705                 710                 715                 720

Pro Gln Asp Arg Leu Thr Glu Val Ile Ala Ser Ile Ile Lys Pro Gln
                                725                 730                 735
```

-continued

Asn Thr Tyr Cys Val Arg Arg Tyr Ala Val Val Gln Lys Ala Ala His
            740                 745                 750

Gly His Val Arg Lys Ala Phe Lys Ser His Val Ser Thr Leu Thr Asp
            755                 760                 765

Leu Gln Pro Tyr Met Arg Gln Phe Val Ala His Leu Gln Glu Thr Ser
    770                 775                 780

Pro Leu Arg Asp Ala Val Val Ile Glu Gln Ser Ser Ser Leu Asn Glu
785                 790                 795                 800

Ala Ser Ser Gly Leu Phe Asp Val Phe Leu Arg Phe Met Cys His His
                805                 810                 815

Ala Val Arg Ile Arg Gly Lys Ser Tyr Val Gln Cys Gln Gly Ile Pro
                820                 825                 830

Gln Gly Ser Ile Leu Ser Thr Leu Leu Cys Ser Leu Cys Tyr Gly Asp
                835                 840                 845

Met Glu Asn Lys Leu Phe Ala Gly Ile Arg Arg Asp Gly Leu Leu Leu
    850                 855                 860

Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
                885                 890                 895

Val Val Asn Leu Arg Lys Thr Val Val Asn Phe Pro Val Glu Asp Glu
                900                 905                 910

Ala Leu Gly Gly Thr Ala Phe Val Gln Met Pro Ala His Gly Leu Phe
                915                 920                 925

Pro Trp Cys Gly Leu Leu Leu Asp Thr Arg Thr Leu Glu Val Gln Ser
    930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
                965                 970                 975

Val Leu Arg Leu Lys Cys His Ser Leu Phe Leu Asp Leu Gln Val Asn
                980                 985                 990

Ser Leu Gln Thr Val Cys Thr Asn Ile Tyr Lys Ile Leu Leu Leu Gln
    995                 1000                1005

Ala Tyr Arg Phe His Ala Cys Val Leu Gln Leu Pro Phe His Gln
    1010                1015                1020

Gln Val Trp Lys Asn Pro Thr Phe Phe Leu Arg Val Ile Ser Asp
    1025                1030                1035

Thr Ala Ser Leu Cys Tyr Ser Ile Leu Lys Ala Lys Asn Ala Gly
    1040                1045                1050

Met Ser Leu Gly Ala Lys Gly Ala Ala Gly Pro Leu Pro Ser Glu
    1055                1060                1065

Ala Val Gln Trp Leu Cys His Gln Ala Phe Leu Leu Lys Leu Thr
    1070                1075                1080

Arg His Arg Val Thr Tyr Val Pro Leu Leu Gly Ser Leu Arg Thr
    1085                1090                1095

Ala Gln Thr Gln Leu Ser Arg Lys Leu Pro Gly Thr Thr Leu Thr
    1100                1105                1110

Ala Leu Glu Ala Ala Ala Asn Pro Ala Leu Pro Ser Asp Phe Lys
    1115                1120                1125

Thr Ile Leu Asp
    1130

<210> SEQ ID NO 3
<211> LENGTH: 23
<212> TYPE: DNA
<213> ORGANISM: Artificial Sequence
<220> FEATURE:
<223> OTHER INFORMATION: FN forward primer

<400> SEQUENCE: 3
caggatcact tacggagaaa cag                                              23

<210> SEQ ID NO 4
<211> LENGTH: 22
<212> TYPE: DNA
<213> ORGANISM: Artificial Sequence
<220> FEATURE:
<223> OTHER INFORMATION: FN reverse primer

<400> SEQUENCE: 4
gccagtgaca gcatacacag tg                                               22

<210> SEQ ID NO 5
<211> LENGTH: 20
<212> TYPE: DNA
<213> ORGANISM: Artificial Sequence
<220> FEATURE:
<223> OTHER INFORMATION: Smad2 forward primer

<400> SEQUENCE: 5
atcctaacag aacttccgcc                                                  20

<210> SEQ ID NO 6
<211> LENGTH: 20
<212> TYPE: DNA
<213> ORGANISM: Artificial Sequence
<220> FEATURE:
<223> OTHER INFORMATION: Smad2 reverse primer

<400> SEQUENCE: 6
ctcagcaaaa acttccccac                                                  20

<210> SEQ ID NO 7
<211> LENGTH: 20
<212> TYPE: DNA
<213> ORGANISM: Artificial Sequence
<220> FEATURE:
<223> OTHER INFORMATION: Smad4 forward primer

<400> SEQUENCE: 7
gcatcgacag agacatacag                                                  20

<210> SEQ ID NO 8
<211> LENGTH: 20
<212> TYPE: DNA
<213> ORGANISM: Artificial Sequence
<220> FEATURE:
<223> OTHER INFORMATION: Smad4 reverse primer

<400> SEQUENCE: 8
caacagtaac aatagggcag                                                  20

<210> SEQ ID NO 9
<211> LENGTH: 21
<212> TYPE: DNA
<213> ORGANISM: Artificial Sequence
<220> FEATURE:
<223> OTHER INFORMATION: GAPDH forward primer

```
<400> SEQUENCE: 9
agggctgctt ttaactctgg t                                              21

<210> SEQ ID NO 10
<211> LENGTH: 21
<212> TYPE: DNA
<213> ORGANISM: Artificial Sequence
<220> FEATURE:
<223> OTHER INFORMATION: GAPDH reverse primer

<400> SEQUENCE: 10
ccccacttga ttttggaggg a                                              21
```